(12) United States Patent
Couvreur et al.

(10) Patent No.: US 11,590,232 B2
(45) Date of Patent: Feb. 28, 2023

(54) BIOCONJUGATES OF NEUROPEPTIDES DERIVATIVES

(71) Applicants: CENTRE NATIONAL DE LA RECHERCHE SCIENTIFIQUE, Paris (FR); UNIVERSITE PARIS-SACLAY, Gif-sur-Yvette (FR)

(72) Inventors: Patrick Couvreur, Paris (FR); Jiao Feng, Chatenay-Malabry (FR); Sinda Lepetre-Mouelhi, Verrières le Buisson (FR)

(73) Assignees: CENTRE NATIONAL DE LA RECHERCHE SCIENTIFIQUE, Paris (FR); UNIVERSITE PARIS-SACLAY, Gif-sur-Yvette (FR)

( * ) Notice: Subject to any disclaimer, the term of this patent is extended or adjusted under 35 U.S.C. 154(b) by 0 days.

(21) Appl. No.: 17/258,701

(22) PCT Filed: Jul. 18, 2019

(86) PCT No.: PCT/EP2019/069333
§ 371 (c)(1),
(2) Date: Jan. 7, 2021

(87) PCT Pub. No.: WO2020/020733
PCT Pub. Date: Jan. 30, 2020

(65) Prior Publication Data
US 2021/0228724 A1    Jul. 29, 2021

(30) Foreign Application Priority Data
Jul. 23, 2018  (EP) .................................... 18306002

(51) Int. Cl.
| A61K 47/54 | (2017.01) |
|---|---|
| A61K 47/69 | (2017.01) |
| A61P 29/02 | (2006.01) |
| A61K 38/00 | (2006.01) |
| C07K 14/665 | (2006.01) |
| C07K 14/70 | (2006.01) |
| A61K 38/33 | (2006.01) |

(52) U.S. Cl.
CPC .............. *A61K 47/54* (2017.08); *A61K 38/33* (2013.01); *A61K 47/6929* (2017.08)

(58) Field of Classification Search
CPC combination set(s) only.
See application file for complete search history.

(56) References Cited

U.S. PATENT DOCUMENTS

| 6,348,211 B1 | 2/2002 | Mantelle et al. |
| 2010/0305030 A1* | 12/2010 | Couvreur .................. A61P 3/10 549/510 |
| 2013/0072438 A1 | 3/2013 | Goldberg |

OTHER PUBLICATIONS

Gopalakrishnan et al., "Lipid-Conjugation of Endogenous Neuropeptides: Improved Biotherapy against Human Pancreatic Cancer," Adv. Healthcare Mater. 4:1015-1022 (2015) supporting information pp. 1-17. (Year: 2015).*
Tamanoi et al., "Farneyslated proteins and cell cycle progression," J cell Biochem Suppl 37:64-70 (2001)) (Year: 2001).*
Extended European Search Report received in European Patent Application No. 18306002.9 dated Jan. 24, 2019.
International Search Report and Written Opinion for PCT/EP2019/069333 dated Oct. 17, 2019.
Feng, J., et al., "A new painkiller nanomedicine to bypass the blood-brain barrier and the use of morphine," Sci. Adv. 5, 2019, pp. 1-12.
Gopalakrishnan, G., et al., "Lipid-Conjugation of Endogenous Neuropeptides: Improved Biotherapy against Human Pancreatic Cancer," Adv. Healthcare Mater. 4, 2015, pp. 1015-1022.
Hong, N., et al., "Conjugates of Enkephalin Analogs: Synthesis and Discrimination of μ and δ Opioid Receptors Based on Membrane Compartment Concept," Bull. Korean Chem. Soc., 2009, vol. 30, No. 3, pp. 599-607.

* cited by examiner

*Primary Examiner* — Julie Ha
*Assistant Examiner* — Kristina M Hellman
(74) *Attorney, Agent, or Firm* — Greer, Burns & Crain, Ltd

(57) ABSTRACT

A bioconjugate comprising at least one neuropeptide covalently bond to at least one hydrocarbon compound of squalene structure.

21 Claims, 6 Drawing Sheets

BIOCONJUGATES OF NEUROPEPTIDES DERIVATIVES

BACKGROUND

The present invention aims to propose novel neuropeptide derivatives, in particular in nanoparticulate form, compositions containing the same and therapeutic uses thereof.

Pain represents an important global health challenge for many reasons, including high prevalence, serious associated sequelae and the relative lack of efficient treatment, especially for neuropathic pain alleviation. Pain relevant disorders such as arthritis, cancer and pathological changes in nervous system are highly prevalent and bring great inconvenience and distress to the patients. Chronic pain has a significant impact not only on the patients themselves, but also on the broader community and economy. By activating μ-opioid receptors, the most powerful and widely used painkillers in current clinical practice are morphine and the related synthetic opioids. But morphinic treatments are associated with severe side effects, such as respiratory depression and addiction linked to the development of opioid tolerance and dependence. According to CDC/NCHS, National Vital Statistics System, every day, more than 115 people in the United States die after overdosing on opioids. The misuse of and addiction to opioids, especially morphine, represents a serious national crisis in the US (and probably also in other countries) that affects public health, as well as, social and economic welfare. This highlights the need to urgently find new pain killers.

In this context, endogenous neuropeptides, such as enkephalin, remain an attractive option. Enkephalins activate both μ- and δ-opioid receptors, but with a ten-fold higher affinity towards δ-opioid receptors. Compared with μ-opioid receptor agonists, δ-opioid receptor ligands are believed to have a much lower abuse potential, as well as, reduced respiratory, gastrointestinal and cognitive impairments. However, enkephalins have historically been limited because of pharmacokinetic issues, and rapid plasma metabolization.

To date, the two main approaches to enhance the analgesic activity of opioid peptides relied on (i) the increase of the stability of endogenous peptides using enkephalinase inhibitors, or (ii) the chemical synthesis of exogenous peptides with enhanced lipophilicity and degradation resistance. However, due to insufficient enzymatic specificity, the enkephalinase inhibitors are often endowed with poorly tolerated side effects. On the other hand, the derivatization of peptides often ends-up with biologically inactive compounds, and the same applies to neuropeptides covalently linked to blood brain barrier transport vectors. This explains why none of the research efforts performed since decades ago has resulted in marketed medicines.

Hence, there is a need for new safe anti-hyperalgesic or analgesic compounds, which are therapeutically effective without generating side effects when they are administered to a subject in need of.

The aim of the present invention is precisely to propose new safe neuropeptides derivatives.

SUMMARY

Thus, according to one of its aspects, the present invention aims to supply novel neuropeptides derivatives that are able to restrict their activity peripherally and to optimize neuropeptide concentration at the site of injury which may overcome these issues.

According to yet another of its aspects, the present invention aims to propose novel neuropeptides derivatives that display increased stability in serum or plasma.

According to yet another of its aspects, the present invention aims to propose novel neuropeptides derivatives that are protected from rapid metabolization and that do not cross the blood brain barrier.

According to yet another of its aspects, the present invention aims to propose novel neuropeptides derivatives that have anti-hyperalgesic properties.

According to another of its aspects, the present invention aims to propose novel neuropeptides derivatives that specifically target peripheral opioid receptors, and thus to prevent and reverse the effects of multiple excitatory agents expressed in damaged tissue.

According to yet another of its aspects, the present invention aims to propose novel neuropeptides derivatives, which evade from the severe side effects associated with the use of morphine or related synthetic opioid. Advantageously, the novel neuropeptides derivatives of the present invention are not associated with respiratory depression and/or addiction.

Finally, according to yet another of its aspects, the present invention aims to propose novel neuropeptides derivatives for effective treatment of pain disorders.

Against all expectations, the present inventors found that the covalent coupling of neuropeptide with at least one specific molecule precisely offers satisfaction in these respects.

Thus, the present invention relates to a bioconjugate comprising at least one neuropeptide covalently bond to at least one hydrocarbon compound of squalene structure (SQ), as represented as follows,

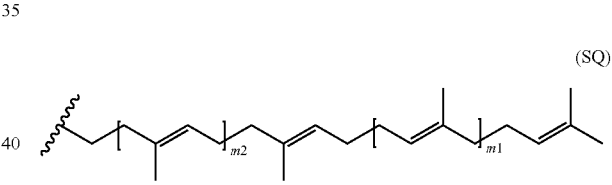

(SQ)

wherein m1 is 0,1,2,3,4,5,6,7,8, or 9, and
m2 is 0,1,2,3,4,5,6,7,8, or 9,
and wherein

represents the bond to the at least one neuropeptide.

In particular, the inventors have shown that the bioconjugates of the invention are able to restrict their activity peripherally and to optimize neuropeptide concentration at the site of injury. By targeting peripheral opioid receptors, the bioconjugates of the invention allow to prevent and reverse the effects of multiple excitatory agents expressed in damaged tissue. Moreover, the inventors have shown that the bioconjugates of the invention provide an effective treatment of pain disorders, without developing the severe side effects associated with the use of morphine or related synthetic opioid, such as respiratory depression and/or addiction.

Within the context of the invention, the term "bioconjugate" refers to the biomolecule, having therapeutic properties, formed upon reaction of the at least one neuropeptide conjugated with the at least one hydrocarbon compound of squalene nature. Within the context of the present invention, the term "conjugated" means that the at least one neuropeptide and the at least one hydrocarbon compound of squalene structure are covalently bond.

Within the context of the invention, the term "squalene structure" is intended to denote a linear or cyclic hydrocarbon-based structure formed from isoprene units. Advantageously, the linear or cyclic hydrocarbon-based structure is formed of at least 2 isoprene units, advantageously formed of at least 3 isoprene units, advantageously formed of at least 4 isoprene units, advantageously formed of at least 5 isoprene units, advantageously formed of at least 6 isoprene units, like squalene, at least or more than 6 isoprene units. In a particular embodiment of the invention, the hydrocarbon compound of squalene structure of the invention is formed of 5 isoprene units. In another particular embodiment of the invention, the hydrocarbon compound of squalene structure of the invention is formed of 6 isoprene units. In another embodiment of the invention, the hydrocarbon compound of squalene structure of the invention is formed of more than 6 isoprene units. In another embodiment of the invention, the hydrocarbon compound of squalene structure of the invention is formed of 7 isoprene units. In another embodiment of the invention, the hydrocarbon compound of squalene structure of the invention is formed of 8 isoprene units. In another embodiment of the invention, the hydrocarbon compound of squalene structure of the invention is formed of 9 isoprene units. In another embodiment of the invention, the hydrocarbon compound of squalene structure of the invention is formed of 10 isoprene units. In another embodiment of the invention, the hydrocarbon compound of squalene structure of the invention is formed of 11 isoprene units. In another embodiment of the invention, the hydrocarbon compound of squalene structure of the invention is formed of 12 isoprene units. In another embodiment of the invention, the hydrocarbon compound of squalene structure of the invention is formed of 13 isoprene units. In another embodiment of the invention, the hydrocarbon compound of squalene structure of the invention is formed of 14 isoprene units. In another embodiment of the invention, the hydrocarbon compound of squalene structure of the invention is formed of 15 isoprene units. In another embodiment of the invention, the hydrocarbon compound of squalene structure of the invention is formed of 16 isoprene units. In another embodiment of the invention, the hydrocarbon compound of squalene structure of the invention is formed of 17 isoprene units. In another embodiment of the invention, the hydrocarbon compound of squalene structure of the invention is formed of 18 isoprene units. In another embodiment of the invention, the hydrocarbon compound of squalene structure of the invention is formed of 19 isoprene units. In another embodiment of the invention, the hydrocarbon compound of squalene structure of the invention is formed of 20 isoprene units.

In a particular embodiment of the invention, the at least one hydrocarbon compound of squalene structure can be represented by the formula (SQ1) as follows:

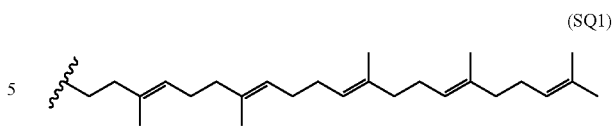

wherein m1 is 2 and m2 is 1 and wherein

represents the bond to the at least one neuropeptide.

In a particular embodiment of the invention, the at least one hydrocarbon compound of squalene structure can be represented by the formula (SQ2) as follows:

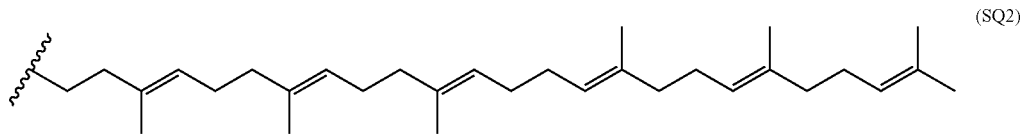

wherein m1 is 2 and m2 is 2 and wherein

represents the bond to the at least one neuropeptide.

As the inventors have found, this squalene structure is particularly important in the context of the present invention since it spontaneously displays, when it is placed in contact with a polar medium and more particularly water, a compacted conformation.

In some embodiments, the term "at least one hydrocarbon compound of squalene structure" refers to one hydrocarbon compound of squalene structure covalently bond to the neuropeptide. In some embodiments, the term "at least one hydrocarbon compound of squalene structure" refers to two hydrocarbon compounds of squalene structure covalently bond to the neuropeptide. In some embodiments, the term "at least one hydrocarbon compound of squalene structure" refers to three hydrocarbon compounds of squalene structure covalently bond to the neuropeptide. In some embodiments, the term "at least one hydrocarbon compound of squalene structure" refers to four hydrocarbon compounds of squalene structure covalently bond to the neuropeptide. In some embodiments, the term "at least one hydrocarbon compound of squalene structure" refers to five hydrocarbon compounds of squalene structure covalently bond to the neuropeptide. In some embodiments, the term "at least one hydrocarbon compound of squalene structure" refers to six or more hydrocarbon compounds of squalene structure covalently bond to the neuropeptide, depending of the size of the neuropeptide.

In a particular advantageously embodiment of the invention, the at least one hydrocarbon compound of squalene structure comprises from 11 to 102 carbon atoms, advantageously from 11 to 32 carbon atoms, advantageously from 11 to 27 carbon atoms.

As illustrations of hydrocarbon-based of squalene structure able to form a bioconjugate of the present invention, we may more particularly mention squalenic acid and derivatives thereof, such as 1,1',2-tris-nor-squalenic acid, 1,1',2-tris-nor-squalenamine, 1,1',2-tris-nor-squalenol, 1,1',2-tris-nor-squalenethiol, squalene acetic acid, squalenylethanol, squalenylethanethiol, squalenylethylamine.

In a particular advantageously embodiment of the invention, the bioconjugate according to the invention contains at least one hydrocarbon compound of squalene structure derived from the molecule of 1,1',2-tris-nor-squalenic acid.

In a particular advantageously embodiment of the invention, the bioconjugate according to the invention contains at least one hydrocarbon compound of squalene structure derived from the molecule of 1,1',2-tris-nor-squalenol.

In a particular advantageously embodiment of the invention, the at least one hydrocarbon compound of squalene structure is 1,1',2-tris-nor-squalenic acid or 1,1',2-tris-nor-squalenol.

Within the context of the invention, the term "neuropeptide" refers to polypeptides or small proteinaceous substances produced and released by neurons through the regulated secretory route and acting on neural substrates. The term "neuropeptide" also refers to small synthetic compound, such as peptidomimetics or analogue of endogenous polypeptides or proteins acting on neural substrates. Advantageously, the at least one neuropeptide is an endogenous neuropeptide.

In some embodiments, the term "at least one neuropeptide" refers to one neuropeptide covalently bond to the hydrocarbon compound of squalene structure. In some embodiments, the term "at least one neuropeptide" refers to two neuropeptides covalently bond to the hydrocarbon compound of squalene structure. In some embodiments, the term "at least one neuropeptide" refers to three neuropeptides covalently bond to the hydrocarbon compound of squalene structure. In some embodiments, the term "at least one neuropeptide" refers to four neuropeptides covalently bond to the hydrocarbon compound of squalene structure.

In some embodiments, the hydrocarbon compound of squalene structure is formed of at least 2 isoprene units, advantageously formed of at least 3 isoprene units, advantageously formed of at least 4 isoprene units, advantageously formed of at least 5 isoprene units, advantageously formed of at least 6 isoprene units, like squalene or more than 6 isoprene units when the hydrocarbon compound of squalene structure is covalently bonded to more than one neuropeptide.

As illustrations of hydrocarbon-based of squalene structure able to covalently bond to two neuropeptides, we may mention the hydrocarbon compound of squalene structure which is represented by the formula (SQ') as follows:

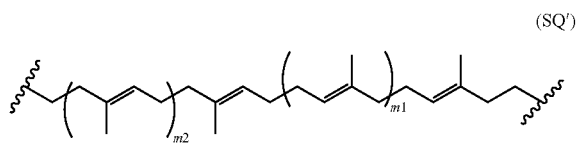

(SQ')

wherein m1 is 0,1,2,3,4,5,6,7,8, or 9, and
m2 is 0,1,2,3,4,5,6,7,8, or 9,
and wherein

represents the bond to the at least one neuropeptide.

In a particular embodiment of the invention, the hydrocarbon compound of squalene structure able to covalently bond to two neuropeptides, can be represented by the formula (SQ'1) as follows:

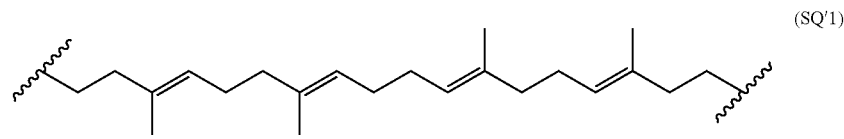 [SMILES: *CC/C(C)=C/CC/C(C)=C/CC/C=C(\C)CC/C=C(\C)CC*]

(SQ'1)

wherein m1 is 2 and m2 is 1 and wherein

represents the bond to the at least one neuropeptide.

In a particular embodiment of the invention, the hydrocarbon compound of squalene structure able to covalently bond to two neuropeptides, can be represented by the formula (SQ'2) as follows:

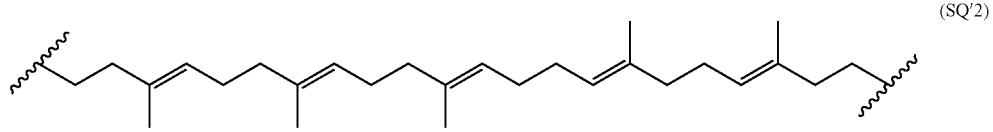 [SMILES: *CC/C(C)=C/CC/C(C)=C/CC/C=C(\C)CC/C=C(\C)CC/C=C(\C)CC*]

(SQ'2)

wherein m1 is 2 and m2 is 2 and wherein represents the bond to the at least one neuropeptide.

In a particularly advantageously embodiment of the invention, the at least one neuropeptide is an opioid peptide. Within the context of the invention, the term "opioid" refers to a natural or synthetic compound that binds to specific opioid receptors in the central nervous system (CNS) and peripheral nervous system (PNS) of a subject, and has agonist (activation) or antagonist (inactivation) effects at these receptors. Opioids may be endogenous (originating within the subject) or exogenous (originating outside of the subject). Opioids that have agonist (activation) effects at opioid receptors produce analgesia. Examples of opioid compounds include, without limitation, opioid alkaloids (e.g., the agonists, morphine and oxycodone, and the antagonists, naloxone and naltrexone) and opioid peptides. In an advantageously embodiment of the invention, the opioid peptide is an endogenous opioid peptide and is selected among the group comprising leucine enkephalin (also called Leu-enkephalin, abbreviated as LENK), methionine enkephalin (also called Met-enkephalin, abbreviated as MENK), dalargin, kyotorphin, endomorphins, endorphins or a derivative thereof.

As used herein, the term "derivative" or "analogue" refers to compound corresponding in structure to the endogenous neuropeptide, but exhibiting some alterations of its structure in comparison with the endogenous neuropeptide. In particular, the term "derivative" or "analogue" includes compound, wherein the amino acid sequence of the neuropeptide or the N-terminal amino acid sequence of the neuropeptide has been altered by the addition, the deletion or the substitution of one or more amino acids selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The term "derivative" or "analogue" also includes compounds, wherein the structure of the neuropeptide can be substituted by one or more aliphatic protective groups, such as methyl, ethyl, propyl, cyclopropyl, butyl, allyl or the like.

In a particularly advantageously embodiment of the invention, the opioid peptide is leucine enkephalin (LENK) or a derivative thereof.

In a particularly advantageously embodiment of the invention, the opioid peptide is methionine enkephalin (MENK) or a derivative thereof.

In a particularly advantageously embodiment of the invention, the opioid peptide is dalargin or a derivative thereof.

In a particularly advantageously embodiment of the invention, the opioid peptide is kyotorphin or a derivative thereof.

In a particularly advantageously embodiment of the invention, the opioid peptide is endomorphins or a derivative thereof.

In a particularly advantageously embodiment of the invention, the opioid peptide is endorphins or a derivative thereof.

In a particular advantageously embodiment of the invention, the bioconjugate according to the invention contains at least one neuropeptide derived from the covalent binding of leucine enkephalin (LENK) or a derivative thereof.

In a particular advantageously embodiment of the invention, the bioconjugate according to the invention contains at least one neuropeptide derived from the covalent binding of methionine enkephalin (MENK) or a derivative thereof.

In a particular advantageously embodiment of the invention, the bioconjugate according to the invention contains at least one neuropeptide derived from the covalent binding of dalargin or a derivative thereof.

In a particular advantageously embodiment of the invention, the bioconjugate according to the invention contains at least one neuropeptide derived from the covalent binding of kyotorphin or a derivative thereof.

In a particular advantageously embodiment of the invention, the bioconjugate according to the invention contains at least one neuropeptide derived from the covalent binding of endomorphins or a derivative thereof.

In a particularly advantageous embodiment of the invention, the bioconjugate according to the invention contains at least one neuropeptide derived from the covalent binding of endorphins or a derivative thereof.

In a particular embodiment of the invention, the bioconjugate comprising at least one neuropeptide covalently bond to at least one hydrocarbon compound of squalene structure as represented by the formula (SQ) as follows:

(SQ)

wherein m1 is 0,1,2,3,4,5,6,7,8, or 9, and
m2 is 0,1,2,3,4,5,6,7,8, or 9,
and wherein represents the bond to the at least one neuropeptide.

Within the context of the invention, the term "bond" associated with the symbol means that symbolizes the site of binding of the at least one hydrocarbon compound of squalene structure to the at least one neuropeptide.

Thus, the binding site may be involved either directly in a single covalent bond between at least one hydrocarbon compound of squalene structure and the at least one neuropeptide, or can be represented by a function resulting from the interaction between two reactive function, for example between a carboxyl function and an alcohol function, a carboxyl function and an amine function, or else can be represented by a spacer. Thus, the at least one neuropeptide and the at least one hydrocarbon compound of squalene structure may be bound either to each other via a covalent bond or via a spacer or a function of the ester, phosphate, disulfure or amide type. Advantageously, the at least one neuropeptide and the at least one hydrocarbon compound of squalene structure may be bound to each other via a spacer.

Within the context of the invention, the term "spacer" means a compound which forms the covalent bond between the at least one neuropeptide and the least one hydrocarbon compound of squalene structure and serves as a connector between the N-terminal amine or the C-terminal acid of the at least one neuropeptide and the least one hydrocarbon compound of squalene structure.

In an advantageously embodiment of the invention, the spacer is selected among the group comprising dioxycarbonyl, diglycolate, carbonate, carbamate and amide spacer.

According to the present invention, the term "carbonate spacer" refers to an organic compound containing the carbonate group —O—(CO)—O—, for its use as a spacer.

According to the present invention, the term "carbamate spacer" refers to an organic compound containing the carbamate group —O—(CO)—NH—, which is used as a spacer. Carbamate spacer also includes substituted carbamate, in which at least one hydrogen of the carbamate has been replaced with a group chosen from alkyl, substituted alkyl, alkenyl, substituted alkenyl, cycloalkyl, substituted cycloalkyl, and polyisoprenyl. Carbamate spacer also includes carbamate ester.

According to the present invention, the term "amide spacer" (—NH—CO—) refers to an organic compound derived from carboxylic acid by replacement of the hydroxyl group —OH by —NH—. The term "amide spacer" includes primary and secondary amides. In the case of secondary amides, the amide can be substituted by alkyl, alkenyl, substituted alkenyl, cycloalkyl, and substituted cycloalkyle and polyisoprenyl. The amide can also be in the form of a 5- or 6-membered heterocycle containing one nitrogen atom.

In a particularly advantageously embodiment of the invention, the spacer is selected among the group comprising dioxycarbonyl, diglycolate and amide spacer.

The formation of the bioconjugate according to the present invention requires that the at least one neuropeptide and the at least one hydrocarbon compound of squalene structure brought into contact respectively bear a so-called reactive function, i.e. able to form the expected covalent bond by their interaction. These functions may or may not be naturally present on the two starting entities. If they are not, the starting entity will have to undergo a modification, prior to the coupling reaction.

More precisely, the hydrocarbon compound of squalene structure according to the invention generally bears a function capable of reacting with a function present on the neuropeptide in question, so as to establish a covalent bond between the two entities, for example of the ester, phosphate, disulfur or amide bond, thus forming a covalent bioconjugate.

Advantageously, the function capable of reacting with a function present on the neuropeptide in question is an acide function or its derivative, in order to form amide bond or ester bond, optionally through a spacer. For example, the hydrocarbon compound of squalene structure able to react with the neuropeptide to form the aforementioned complex is 1,1',2-tris-nor-squalenic acid or a derivative thereof, for example its anhydride mixed with ethyl chloroformate. Preferably, the acid chloride derived from 1,1',2-tris-nor-squalenic acid is used.

According to another variant, it is an alcohol function. For example, the hydrocarbon compound of squalene structure able to react with a neuropeptide, optionally through a spacer to form the aforementioned conjugate is 1,1',2-tris-nor-squalenol derived from 1,1',2-tris-norsqualenol aldehyde (reduction by $LiAlH_4$).

According to another embodiment, the covalent bond that exists between the two types of molecules may be represented by a spacer. In a particularly advantageous embodiment of the invention, the bioconjugate of the invention comprises the at least one neuropeptide covalently bond to the at least one hydrocarbon compound of squalene structure, wherein the at least one neuropeptide and the at least one hydrocarbon compound of squalene structure are bound to each other via a spacer.

Advantageously, the bioconjugate of the invention comprises the at least one neuropeptide covalently bond to the at least one hydrocarbon compound of squalene structure, wherein the at least one neuropeptide and the at least one hydrocarbon compound of squalene structure are bound to each other via a spacer, the spacer being selected among the group comprising dioxycarbonyl, diglycolate, carbonate, carbamate and amide spacer.

Advantageously, the bioconjugate of the invention comprises the at least one neuropeptide covalently bond to the at least one hydrocarbon compound of squalene structure, wherein the C-terminal acid of the at least one neuropeptide and the at least one hydrocarbon compound of squalene structure are covalently bond by using dioxycarbonyl spacer.

Advantageously, the bioconjugate of the invention comprises the at least one neuropeptide covalently bound to the at least one hydrocarbon compound of squalene structure, wherein the N-terminal amine of the at least one neuropeptide and the at least one hydrocarbon compound of squalene structure are covalently bond by using diglycolate spacer.

Advantageously, the bioconjugate of the invention comprises the at least one neuropeptide covalently bound to the at least one hydrocarbon compound of squalene structure, wherein the N-terminal amine of the at least one neuropeptide and the at least one hydrocarbon compound of squalene structure are covalently bond by using amide spacer.

The coupling reaction necessary for establishing at least one covalent bond between the at least one neuropeptide and the at least one hydrocarbon compound of squalene structure according to the present invention may be carried out in standard conditions and its implementation is therefore clearly part of the knowledge of a person skilled in the art. This reaction is generally carried out in solution in the presence of at least one hydrocarbon compound of squalene structure considered according to the present invention with respect to the neuropeptide employed according to the present invention, in the standard conditions required for causing interaction of the C-terminal acid or the N-terminal amine of the at least one neuropeptide and the reactive function of the at least one hydrocarbon compound of squalene structure.

Advantageously, a starting hydrocarbon compound of squalene structure for synthesis of the bioconjugate according to the present invention is a squalenic acid, such as for example 1,1',2-tris-nor-squalenic acid, which may be prepared by oxidation of 1,1',2-tris-nor-squalenic aldehyde by Jone's reagent.

Advantageously, another starting hydrocarbon compound of squalene structure for synthesis of the bioconjugate according to the present invention is a squalenic acid derivative, such as for example 1,1',2-tris-nor-squalenol, which may be prepared by reduction of 1,1',2-tris-nor-squalenaldehyde by LiAlH₄.

In a particularly advantageously embodiment of the invention, the bioconjugate of the invention is chosen from:

contacting 1,1',2-tris-nor-squalenic acid with chromethyl chlorosulfate to obtain a chloromethyl ester of 1,1',2-tris-nor-squalenic acid, protecting the N-terminal amine of the Leucine-enkephalin with an Alloc group, submitting the carboxylate function of the Leucine-enkephalin to an alkylation reaction with the chloromethyl ester of 1,1',2-tris-nor-squalenic acid,

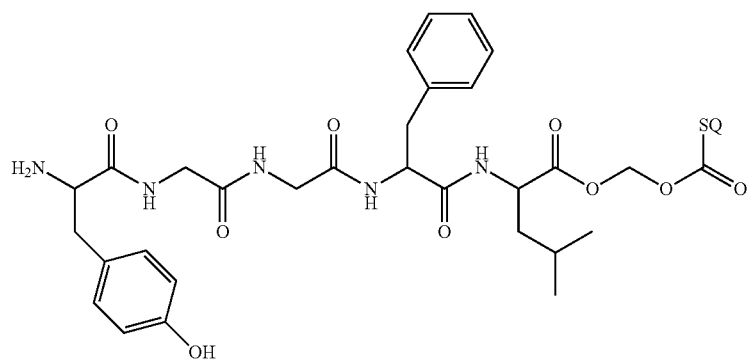

1

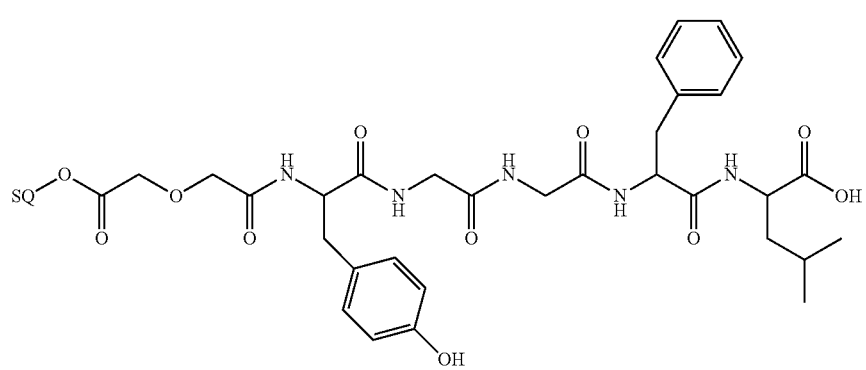

2

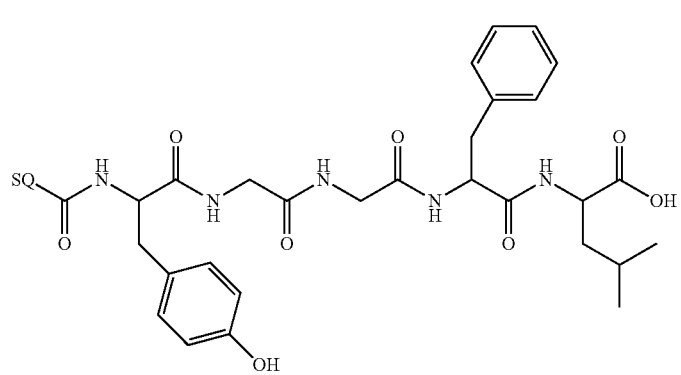

3

Advantageously, the bioconjugate (1) of the invention comprises Leucine-enkephalin covalently bond to 1,1',2-tris-nor-squalenic acid by using a dioxycarbonyl spacer.

Advantageously, the bioconjugate (2) of the invention comprises Leucine-enkephalin covalently bond to 1,1',2-tris-nor-squalenol, by using a diglycolate spacer.

Advantageously, the bioconjugate (3) of the invention comprises Leucine-enkephalin covalently bond to 1,1',2-tris-nor-squalenic acid, by using an amide spacer.

The bioconjugate of the invention can be synthetized by methods that are well known by a person skilled in the art.

Advantageously, the bioconjugate (1) according to the present invention is synthetized by:

deprotecting the N-terminal amine of the Leucine-enkephalin to obtain the bioconjugate (1).

The method for preparing the bioconjugate (1) according to the invention make it possible to obtain amount of said bioconjugate (1) with a yield of at least 9%, advantageously 9,5%

Advantageously, the bioconjugate (2) according to the present invention is synthetized by:

contacting 1,1',2-tris-nor-squalenol with diglycolic anhydride to obtain a solution of squalene-diglycolic acid, submitting the amine function of the Leucine-enkephalin to a condensation reaction with the solution of squalene-diglycolic acid to obtain the bioconjugate (2).

The method for preparing the bioconjugate (2) according to the invention make it possible to obtain amount of said bioconjugate (2) with a yield of at least 60%, advantageously 69%

Advantageously, the bioconjugate (3) according to the present invention is synthetized by:
- acid activation of 1,1',2-tris-nor-squalenic acid using ethyl chloroformate to obtain a solution of mixed anhydride of squalene,
- submitting the amine function of the Leucine-enkephalin to a condensation reaction with the solution of mixed anhydride of squalene to obtain the bioconjugate (3).

The method for preparing the bioconjugate (3) according to the invention make it possible to obtain amount of said bioconjugate (3) with a yield of at least 70%, advantageously 73%

Another aspect of the invention concerns the bioconjugate as defined above for use as a drug, preferably as an anti-hyperalgesic drug.

According to the invention, the bioconjugate of the invention is particularly useful for reducing thermal hyperalgesia and has a longer anti-hyperalgesic effect compared with morphine treatment.

According to the invention, the bioconjugate is particularly useful for treating pain disorders. As used herein, the term "treatment" or "curative treatment" or "alleviation" is defined as a treatment leading to a cure or a treatment which alleviates, improves and/or eliminates, reduces and/or stabilizes the symptoms of a disease or the suffering that it causes.

Advantageously, pain disorders include peripheral and central pain. Within the context of the present invention, peripheral pain includes nociceptive pain, inflammatory pain and neuropathic pain.

Within the context of the present invention, nociceptive pain refers to as physiological pain and serves as a defense mechanism throughout the animal kingdom. Within the context of the present invention, inflammatory pain, arising from severe wounds and/or associated with inflammatory infiltrates, can be well controlled by non-steroidal anti-inflammatory drugs (NSAID)-like drugs, steroids and opiates. Within the context of the present invention, neuropathic pain is thought to arise from inherent defects in sensory and as a consequence in sympathetic neurons and can be secondary to trauma.

According to the present invention, pain disorders include pain elicited from tissue injury, e.g., inflammation, infection, ischemia, pain associated with musculoskeletal disorders (e.g. joint pain, tooth pain), headaches (e.g., migrane), pain associated with surgery, pain related to inflammation (e.g. irritable bowel syndrome or arthritis), or chest pain.

According to the present invention, pain disorders also include complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, arthritis, rheumatoid polyarthritis, Bechterew's disease, fibromyalgia, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia.

According to the present invention, pain disorders also include cancer pain, such as pain associated with brain cancer, bone cancer, lung cancer or prostate cancer.

In an advantageously embodiment of the invention, the bioconjugate of the invention is particularly useful for treating pain disorders, in particular peripheral and central pain. In a particularly advantageously embodiment of the invention, the bioconjugate of the invention is particularly useful for treating peripheral pain such as nociceptive pain, inflammatory pain, neuropathic pain.

In a more particularly advantageously embodiment of the invention, the bioconjugate of the invention is particularly useful for treating pain disorders including pain elicited from tissue injury, e.g., inflammation, infection, ischemia; pain associated with musculoskeletal disorders (e.g. joint pain, tooth pain), headaches (e.g., migrane), pain associated with surgery, pain related to inflammation (e.g. irritable bowel syndrome or arthritis), chest pain, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, arthritis, rheumatoid polyarthritis, Bechterew's disease, fibromyalgia, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, pain asymbolia and cancer pain, such as pain associated with brain cancer, bone cancer, lung cancer or prostate cancer.

Another aspect of the invention relates to a nanoparticle comprising the bioconjugate as defined above.

Against all expectations, the inventors found that the bioconjugate formed by covalent coupling of at least one neuropeptide considered according to the invention with at one hydrocarbon compound of squalene structure in the sense of the invention displays capacity for self-organizing in a compact form in a polar solvent medium, and thus leads to the formation of nanoparticles.

Thus, according to another of its aspects, the present invention relates to nanoparticle of the bioconjugate according to the invention.

In an advantageously embodiment of the invention, the nanoparticles thus obtained have a mean diameter in the range from 10 nm to 500 nm, advantageously from 10 nm to 250 nm, advantageously from 10 nm to 200 nm, advantageously from 60 nm to 120 nm, advantageously from 61 nm to 112 nm measured by dynamic light scattering using the Zetasizer Nano (a Registered trademark of Malvern), Malvern Instrument, United Kingdom. Advantageously, the nanoparticles have mean diameter comprised between 10 and 500 nm, between 10 and 250 nm, between 10 and 200 nm, advantageously between 60 and 120 nm, advantageously between 61 and 112 nm.

Thus, these particles have a size that proves compatible with any method of administration, in particular oral, parenteral, intramuscular, intranasal, sublingual, intratracheal, inhalation, ocular, vaginal, rectal, intracapsular, intravenous, transdermal and intraperitoneal administration.

As stated above, the nanoparticulate formulation is advantageous, in that it notably prevents the at least one neuropeptide from plasma degradation and confers to the neuropeptide a significant anti-hyperalgesic effect which lasted longer than after treatment with morphine. Nanoparticulate formulation further allows the specific delivery of the neuropeptide into inflamed tissues for pain control.

The nanoparticles according to the invention are, of course, able to carry a multitude of reactive functions on their surface, such as carboxyl or amine functions for example. It is therefore conceivable to fix ail kinds of molecules to these functions, notably by covalent bonds.

As illustrative, non-limiting examples of molecules of this type that may be associated with the nanoparticles, we may notably mention molecules of the marker type (ie. any fluorescent probe or a probe emitting in the near-infrared like bodipy-cholesterol or DiIC18), MRI contrast agent (ie. Gadolinium or iron oxide), compounds able to provide a targeting function, as well as any compound able to endow them with particular pharmacokinetic characteristics.

Regarding this last-mentioned aspect, we may thus envisage fixing, on the surface of these nanoparticles, lipophilic derivatives of polyethylene glycol, for example the polyethylene glycol/cholesterol conjugate, polyethylene glycol-phosphatidylethanolamine or better still polyethylene glycol/squalene. In fact, taking into account the natural affinity of the squalene residues for one another, the polyethylene glycol/squalene conjugate combines, in the present case, with the nanoparticles according to the invention, and thus leads to the formation of nanoparticles with a surface coating of polyethylene glycol. Moreover, as already mentioned, during the process of formation of the nanoparticles according to the invention, the polyethylene glycol/squalene conjugate advantageously acts as surfactant owing to its amphiphilic behavior and therefore stabilizes the colloidal suspension, thus reducing the size of the nanoparticles formed.

In a particularly advantageous embodiment, the nanoparticle comprising the bioconjugate as defined above, may further comprises an anti-inflammatory compound. As illustrative, non-limiting examples of anti-inflammatory compound can be cortisone, hydrocortisone, dexamethasone, prednisone, prednisolone, indomethacine and any other AINS.

According to an advantageous embodiment, the nanoparticles according to the invention are formulated as an aqueous dispersion.

According to another advantageous embodiment, the nanoparticles according to the invention are in the form of lyophilizate.

Advantageously, they are nanoparticles of at least one neuropeptide and at one hydrocarbon compound of squalene structure covalently bond by a spacer as defined above.

They may also advantageously be nanoparticles of Leucine-enkephalin-squalene with dioxycarbonyl spacer or Leucine-enkephalin-squalene with diglycolic spacer or Leucine-enkephalin-squalene with amide spacer.

More precisely, the nanoparticles are formed by bringing the bioconjugate into contact with an aqueous medium in favorable conditions for its agglomeration in the form of nanoparticles. They may notably be so-called methods of nanoprecipitation or methods of emulsion/solvent evaporation.

The nanoparticles according to the present invention may advantageously be obtained as follows. A bioconjugate according to the invention is dispersed in at least one organic solvent (for example an alcohol such as ethanol, or acetone) at a concentration sufficient to obtain, on adding the resultant mixture, with stirring, and generally dropwise, to an aqueous phase, the instantaneous formation of nanoparticles according to the invention in suspension in said aqueous phase. If applicable, said nanoparticles are isolated by techniques that are well known by a person skilled in the art.

In a particular embodiment of the present invention, the at least one organic solvent can be ethanol and the concentration of the at least one organic solvent is comprised between 1 mg/ml and 10 mg/ml, advantageously between 6 mg/ml and 9 mg/ml, advantageously between 7 mg/m and 9 mg/ml, advantageously the concentration of the at least one organic solvent is 8 mg/ml.

In a particular embodiment of the present invention, the aqueous phase can be an aqueous dextrose solution, advantageously a 5% aqueous dextrose solution. At the end, the organic solvent is eliminated by evaporation under vacuum.

Nanoprecipitation on may generally be carried out at room temperature. However, the application temperature must not affect the activity of the neuropeptide in question. The method of preparing the nanoparticles according to the invention is particularly advantageous, in that it does not require the obligatory presence of surfactants. In other words, the nanoprecipitation is performed in absence of surfactant. This property is particularly desirable, as a great numerous surfactants are not compatible with application in vivo. Thus, another advantage of the present invention is that no potentially toxic organic solvent or surfactant is required for production of said compositions according to the invention. However, it is to be understood that the use of surfactants, generally advantageously devoid of any toxicity, is conceivable in the context of the invention. Surfactants of this type may moreover allow even smaller sizes to be attained during nanoparticle formation. As illustrative, non-limiting examples of surfactants of this type that may be used in the present invention, we may notably mention polyoxyethylene-poly-oxypropylene copolymers, phospholipids derivatives and lipophilic derivatives of polyethylene glycol. As a lipophilic derivative of polyethylene glycol, we may mention for example polyethylene glycol cholesterol. As examples of the polyoxyethylene-polyoxypropylene block copolymers, we may mention in particular the polyoxyethylene-polyoxypropylene-polyoxyethylene triblock copolymers, also called Poloxamers®, Pluronics® or synperonics, which are marketed, notably, by the company BASF. Related to these families of copolymers, the poloxamines, which consist of hydrophobic segments (based on polyoxypropylene), hydrophilic segments (based on polyoxyethylene) and a central part derived from the ethylenediamine unit, may also be used.

Another aspect of the invention relates to a pharmaceutical composition comprising the bioconjugate as defined above, optionally in form of a nanoparticle as active substance, and at least one pharmaceutically acceptable excipient and/or carrier. In particular embodiment, the invention concerns a pharmaceutical composition comprising a pharmaceutically effective amount of the bioconjugate as defined above, optionally in form of a nanoparticle as active substance and at least one pharmaceutically acceptable excipient or carrier.

In particularly advantageous embodiment of the present invention, the pharmaceutical composition according to the invention is particularly useful for treating pain disorders.

In one embodiment the subject is a human. In another embodiment the subject is a non-human animal, e.g., a dog, cat, horse, cow, pig, sheep, goat or primate.

According to embodiments that involve administering to a subject in need of treatment a therapeutically effective amount of the bioconjugate, optionally in form of a nanoparticle, as provided herein, "therapeutically effective" or "an amount effective to treat" or "pharmaceutically effective" denotes the amount of bioconjugate or of a composition needed to inhibit or reverse a disease condition (e.g., to treat pain disorders). Determining a therapeutically effective amount specifically depends on such factors as toxicity and efficacy of the medicament. These factors will differ depending on other factors such as potency, relative bioavailability, subject body weight, severity of adverse side-effects and preferred mode of administration. Toxicity may be determined using methods well known in the art. Efficacy may be determined utilizing the same guidance. Efficacy can be measured by a decrease of pain, for example, in a carrageenan-induced paw edema model in rats (Hargreaves test). A pharmaceutically effective amount, therefore, is an amount that is deemed by the clinician to be toxicologically tolerable, yet efficacious.

Dosage may be adjusted appropriately to achieve desired drug (e.g., bioconjugate of the invention, optionally in form of nanoparticle) levels, local or systemic, depending upon the mode of administration. In the event that the response in a subject is insufficient at such doses, even higher doses (or effective higher doses by a different, more localized delivery route) may be employed to the extent that subject tolerance permits. Multiple doses per day may also be employed to achieve appropriate systemic levels of neuropeptide. Appropriate systemic levels can be determined by, for example, measurement of the subject's peak or sustained plasma level of the drug. "Dose" and "dosage" are used interchangeably herein.

In some embodiments, the amount of bioconjugate, optionally in form of nanoparticle or pharmaceutical composition comprising the bioconjugate as active substance administered to a subject is 1 mg to 100 mg/kg, depending on pain intensity. Of course, this unit dose may be repeated when needed.

In some embodiments, the pharmaceutical compositions provided are employed for in vivo applications. Depending on the intended mode of administration in vivo the pharmaceutical compositions used may be in the dosage form of solid, semi-solid or liquid such as, e.g., tablets, pills, powders, capsules, gels, ointments, liquids, suspensions, or the like. Preferably, the pharmaceutical compositions are administered in unit dosage forms suitable for single administration of precise dosage amounts. The pharmaceutical compositions may also include, depending on the formulation desired, at least one pharmaceutically acceptable carrier or diluent, which are defined as aqueous-based vehicles commonly used to formulate pharmaceutical compositions for animal or human administration. The diluent is selected so as not to affect the biological activity of the specific binding molecule or the fusion protein of interest. Examples of such diluents are distilled water, physiological saline, Ringer's solution, dextrose solution, and Hank's solution. The same diluents may be used to reconstitute a lyophilized recombinant protein of interest. In addition, the pharmaceutical composition may also include other medicinal agents, pharmaceutical agents, carriers, adjuvants, nontoxic, non-therapeutic, non-immunogenic stabilizers, etc. Effective amounts of such diluent or carrier are amounts which are effective to obtain a pharmaceutically acceptable formulation in terms of solubility of components, biological activity, etc. In some embodiments the pharmaceutical compositions provided herein are sterile.

Administration during in vivo treatment may be by any routes, including oral, parenteral, transdermal, intramuscular, intranasal, sublingual, intratracheal, inhalation, ocular, vaginal, and rectal. Intracapsular, intravenous, and intraperitoneal routes of administration may also be employed.

The skilled artisan recognizes that the route of administration varies depending on the disorder to be treated. For example, the pharmaceutical compositions or bioconjugate, optionally in form of nanoparticles herein may be administered to a subject via oral, parenteral or topical administration. In one embodiment, the pharmaceutical compositions or bioconjugate, optionally in form of nanoparticles herein are administered by intravenous infusion.

The pharmaceutical compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulating agents such as suspending, stabilizing and/or dispersing agents.

Pharmaceutical formulations for parenteral administration include aqueous solutions of the active pharmaceutical compositions in water soluble form. Additionally, suspensions of the active pharmaceutical compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the pharmaceutical compositions to allow for the preparation of highly concentrated solutions. Alternatively, the active compositions may be in powder form for constitution with a suitable vehicle, e.g., sterile pyrogen-free water, before use.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Also desired is the increase in overall stability of the neuropeptide and increase in circulation time in the body. Examples of such molecules include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. Preferred for pharmaceutical usage, as indicated above, are polyethylene glycol molecules. For oral compositions, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment or by release of the biologically active material beyond the stomach environment, such as in the intestine.

For buccal administration, the compositions may take the form of tablets or lozenges formulated in conventional manner.

For administration by inhalation, the compositions for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compositions and a suitable powder base such as lactose or starch.

Also contemplated herein is pulmonary delivery. The pharmaceutical compositions can be delivered to the lungs of a mammal while inhaling and traverses across the lung epithelial lining to the blood stream. Contemplated for use in the practice of this disclosure are a wide range of mechanical devices designed for pulmonary delivery of therapeutic products, including but not limited to nebulizers, metered dose inhalers, and powder inhalers, all of which are familiar to those skilled in the art.

Nasal delivery of a pharmaceutical composition disclosed herein is also contemplated. Nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextrin, as well as, bioadhesive excipients like for instance chitosan.

The pharmaceutical compositions may also be formulated in rectal or vaginal compositions such as suppositories or retention enemas, e.g., containing conventional suppository bases such as cocoa butter or other glycerides.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, dermal or transdermal patches, drops or preparations with protracted release of active compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

We may envisage formulating at least one bioconjugate and/or nanoparticles according to the present invention at a rate from 0.1 to 10 wt %, expressed as weight of neuropeptide active substance, or even more, relative to the total weight of the considered pharmaceutical composition.

In particularly advantageous embodiment of the present invention, the pharmaceutical composition according to the invention solely comprises the bioconjugate as defined above, optionally in form of a nanoparticle as the unique active substance.

In another advantageous embodiment of the present invention, the pharmaceutical composition comprising the bioconjugate as defined above, optionally in form of a nanoparticle may further comprised one or more active substances, such as anti-inflammatory compound, which can synergistically interact with the bioconjugate.

Another subject of the invention relates to a method for the preventative treatment of pain disorders in patients in need of, comprising the administration to said patients of the bioconjugate as defined above, optionally in form of a nanoparticle, as active substance or a pharmaceutical composition comprising a therapeutically effective amount the bioconjugate as defined above, optionally in form of a nanoparticle, as active substance and at least one pharmaceutically acceptable excipient and/or carrier as defined above. More preferably, the pain disorders includes pain elicited from tissue injury, e.g., inflammation, infection, ischemia; pain associated with musculoskeletal disorders (e.g. joint pain, tooth pain), headaches (e.g., migraine), pain associated with surgery, pain related to inflammation (e.g. irritable bowel syndrome or arthritis), chest pain, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, arthritis, rheumatoid polyarthritis, Bechterew's disease, fibromyalgia, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, pain asymbolia and cancer pain, such as pain associated with brain cancer, bone cancer, lung cancer, prostate cancer or pain induced by anti-cancer treatment.

Within the context of the invention, the term "prevention" or "prophylaxis" or "preventative treatment" or "prophylactic treatment" comprises a treatment leading to the prevention of a disease as well as a treatment reducing and/or delaying the incidence of a disease or the risk of it occurring.

In a particular advantageous embodiment, the present invention relates to the use of a pharmaceutical composition comprising a therapeutically effective amount of the bioconjugate as defined above, optionally in form of a nanoparticle, as active substance in the manufacture of a medicinal product intended for the prevention of pain disorders.

In a particular advantageous embodiment, the present invention relates to the use of a pharmaceutical composition comprising a therapeutically effective amount of the bioconjugate as defined above, optionally in form of a nanoparticle, as active substance in the manufacture of a medicinal product intended for the prevention of pain disorders, selected among the group comprising pain elicited from tissue injury, e.g., inflammation, infection, ischemia; pain associated with musculoskeletal disorders (e.g. joint pain, tooth pain), headaches (e.g., migraine), pain associated with surgery, pain related to inflammation (e.g. irritable bowel syndrome or arthritis), chest pain, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, arthritis, rheumatoid polyarthritis, Bechterew's disease, fibromyalgia, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, pain asymbolia and cancer pain, such as pain associated with brain cancer, bone cancer, lung cancer, prostate cancer or pain induced by anti-cancer treatment.

Another subject of the invention relates to a method for treating pain disorders in patients in need of, comprising the administration to said patients of the bioconjugate as defined above, optionally in form of a nanoparticle, as active substance, or a pharmaceutical composition comprising a therapeutically effective amount of the bioconjugate as defined above, optionally in form of a nanoparticle, as active substance, and at least one pharmaceutically acceptable excipient and/or carrier as defined above. More preferably, the pain disorders includes pain elicited from tissue injury, e.g., inflammation, infection, ischemia; pain associated with musculoskeletal disorders (e.g. joint pain, tooth pain), headaches (e.g., migrane), pain associated with surgery, pain related to inflammation (e.g. irritable bowel syndrome or arthritis), chest pain, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, arthritis, rheumatoid polyarthritis, Bechterew's disease, fibromyalgia, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, pain asymbolia and cancer pain, such as pain associated with brain cancer, bone cancer, lung cancer, prostate cancer or pain induced by anti-cancer treatment.

In a particular advantageous embodiment, the present invention relates to the use of a pharmaceutical composition comprising a therapeutically effective amount of the bioconjugate as defined above, optionally in form of a nanoparticle, as active substance, in the manufacture of a medicinal product intended for the treatment of pain disorders.

In a particular advantageous embodiment, the present invention relates to the use of a pharmaceutical composition comprising a therapeutically effective amount of the bioconjugate as defined above, optionally in form of a nanoparticle, as active substance, in the manufacture of a medicinal product intended for the treatment of pain disorders, selected among the group comprising pain elicited from tissue injury, e.g., inflammation, infection, ischemia; pain associated with musculoskeletal disorders (e.g. joint pain, tooth pain), headaches (e.g., migrane), pain associated with surgery, pain related to inflammation (e.g. irritable bowel syndrome or arthritis), chest pain, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, arthritis, rheumatoid polyarthritis, Bechterew's disease, fibromyalgia, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, pain asymbolia and cancer pain, such as pain associated with brain cancer, bone cancer, lung cancer, prostate cancer or pain induced by anti-cancer treatment.

Another aspect of the invention relates to a patch comprising the bioconjugate, optionally in form of nanoparticle as defined above. AS used herein, the term "patch" or "transdermal patch" refers to a pad containing the bioconjugate of the invention, optionally in form of nanoparticle, to be placed on the exterior surface of a patient for absorption of the active substance into the bloodstream, skin or underlying tissue.

The patch is typically placed on the skin and the bioconjugate of the invention, optionally in form of nanoparticle, is released gradually from the patch over time. The patch may be an adhesive patch.

The patch may be designed to deliver the bioconjugate, optionally in form of nanoparticle to the subject at any suitable rate. As demonstrated in U.S. Pat. No. 6,348,211 (Juan Mantelle et al), among others, the desired delivery rate can be achieved by varying the selection of ingredients, the amount of the ingredients, how the formulation is made, and other formulation process parameters.

In some embodiments, the transdermal patch delivers at least 1 mg of the active agent transdermally to the subject over at least 30 minutes, advantageously at least one hour, advantageously at least 2 hours, advantageously at least 3 hours, advantageously at least 4 hours, advantageously at least 5 hours, advantageously at least 6 hours, advantageously at least 7 hours, advantageously at least 8 hours, advantageously at least 9 hours, advantageously at least 10 hours, advantageously at least 11 hours, advantageously at least 12 hours, advantageously at least 13 hours, advantageously at least 14 hours, advantageously at least 15 hours, advantageously at least 16 hours, advantageously at least 17 hours, advantageously at least 18 hours, advantageously at least 19 hours, advantageously at least 20 hours, advantageously at least 21 hours, advantageously at least 22 hours, advantageously at least 23 hours, advantageously at least 24 hours, after applying the patch; in some cases, 5-175 mg; and in some cases, 5-120 mg.

The patch comprises a drug-containing layer, which comprises the bioconjugate, optionally in form of nanoparticle. In addition to the bioconjugate, optionally in form of nanoparticle, the drug-containing layer comprises a carrier material for carrying the active agent. The active agent is mixed with the carrier material (e.g. blended, dispersed therein, encapsulated therein, etc.). In general, the carrier material comprises ingredients that are suitable for transdermal drug delivery, such as adhesives, solvents, additives, adjuvants, plasticizers, tackifiers, skin penetration enhancers, crosslinking agents, or other excipient substances.

The bioconjugate, optionally in form of nanoparticle can be admixed in the carrier material in any suitable way, including homogeneous admixtures, heterogeneous admixtures, or a combination thereof. For example, the drug may be homogenously dispersed in the drug-containing layer. In another example, the drug may form microspheres within a crosslinked polymer matrix of the drug-containing layer.

In a particularly advantageous embodiment of the present invention, the patch comprising the bioconjugate, optionally in form of nanoparticle as defined above can be a patch equipped with micro-needles.

Another aspect of the invention relates to a patch comprising the bioconjugate, optionally in form of nanoparticle as defined above for its use in the treatment of pain disorders.

DETAILED DESCRIPTION

Examples

Figure 1:
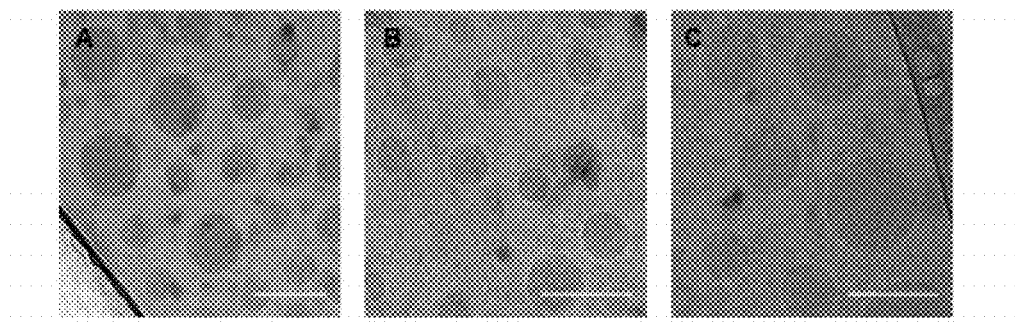
FIG. 1 shows the NPs characterization. Representative Cryo-TEM images showing the formation of NPs from different bioconjugates: (A) LENK-SQ-Diox NPs, (B) LENK-SQ-Dig NPs, and (C) LENK-SQ-Am NPs at a concentration of 4 mg/ml in Milli-Q water. Scale bars=100 nm. Physicochemical characteristics of NPs (ie. size, polydispersity index (PDI), zeta potential and % drug loading) are shown in the table.

Example 1: Synthesis of the
Leu-Enkephalin-Squalene Bioconjugate with
Dioxycarbonyl Spacer (LENK-SQ-Diox)

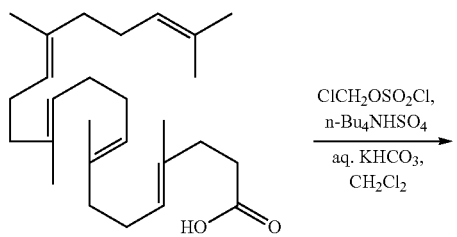

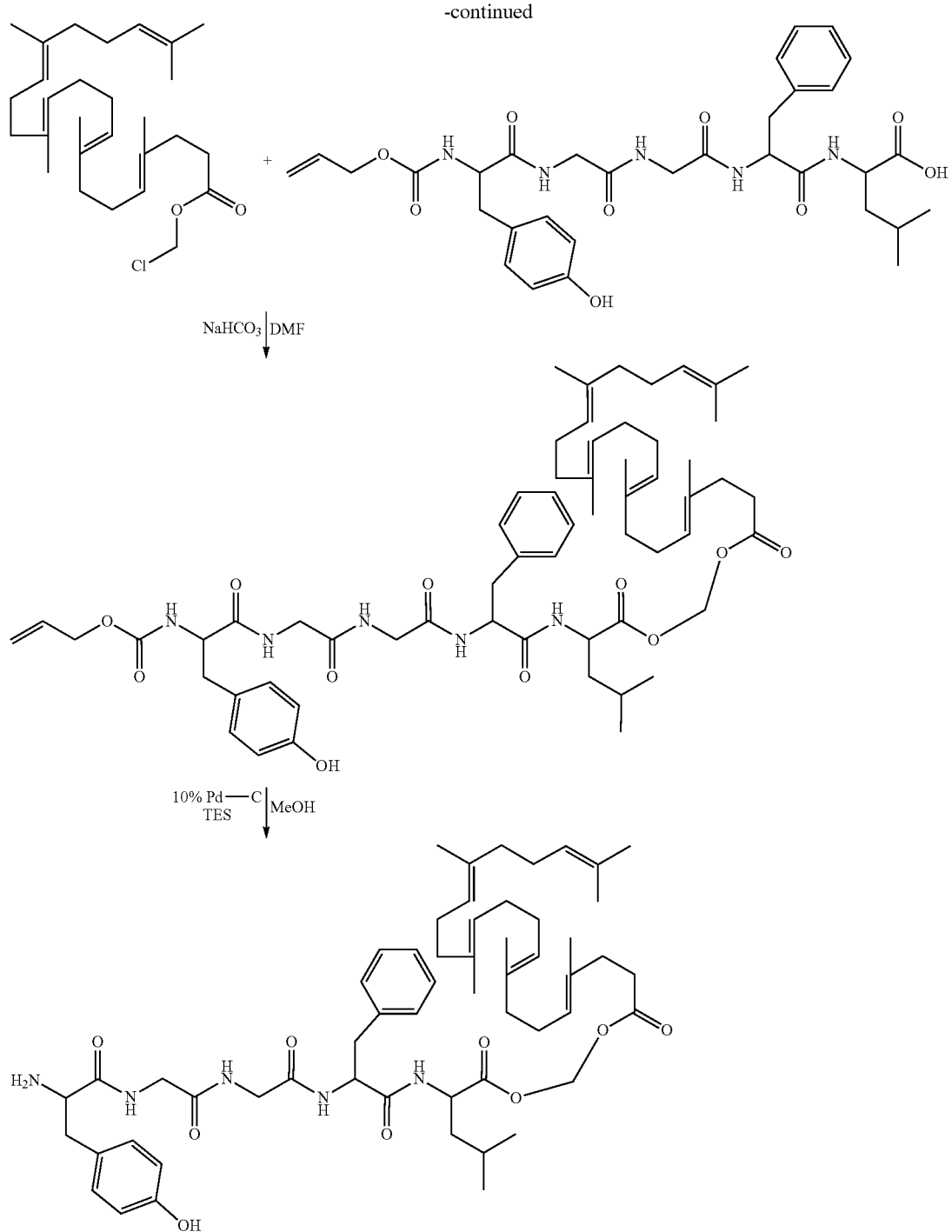

1. Synthesis of 1,1',2-tris-norsqualenic acid chloromethyl ester 1,1',2-tris-norsqualenic acid was synthesized by oxidation of 1,1',2-tris-norsqualenic aldehyde by Jone's reagent as previously reported (35, 36). To a solution of 1,1',2-tris-norsqualenic acid (400 mg, 1 mmol) and n-Bu4NHSO4 (34 mg, 0.1 mmol) in DCM (2 mL) was added a solution of KHCO3 (300 mg, 3.0 mmol) in water (2 mL). The reaction mixture was vigorously stirred, and chloromethyl chlorosulfate (185 mg, 1.15 mmol) was added dropwise. After stirring for 1 h, DCM (10 mL) was added to extract the product. The organic phase was separated, washed with brine, dried over magnesium sulfate, and concentrated under reduced pressure to afford a pale yellow oil which was used in the following step without further purification.

2. Synthesis of Alloc-Leu-enkephalin-squalene (Alloc-LENK-SQ-Diox)

The 1,1', 2-tris-norsqualenic acid chloromethyl ester (200 mg, 0.445 mmol) was added into a mixture of Alloc-LENK (285 mg, 0.445 mmol) and NaHCO$_3$(37 mg, 0.4 mmol) in 3 mL DMF. The reaction mixture was stirred at 40° C. under argon for 4 days. The final reaction mixture was concentrated in vacuo, and the residue was purified by flash column chromatography on silica gel DCM/EtOH (100:0 to 97:3) to afford the title compound as a yellow oil (168 mg, 40% yield).

3. Synthesis of Leu-enkephalin-squalene (LENK-SQ-Diox)

To a stirred solution of Alloc-LENK-SQ (110 mg, 0.1 mmol) and 10% Pd—C(20% by weight of Alloc-LENK-SQ-Diox) in MeOH (11 mL) was added dropwise neat triethylsilane (TES) (1215 mg, 10 mmol) under argon. When the reaction was completed, the mixture was filtered through celite to remove the Pd—C, and the residual TES and solvent were removed by evaporation. The residue was first purified by flash column chromatography on silica gel with DCM/EtOH (90/10). The resulting product was dissolved in 200 µL of ethanol prior to undergo a second purification by semi-preparative reverse-phase HPLC (RP-HPLC) system (Waters, Ma 01757, USA) on a uptisphere C18 column (100×21.2 mm, pore size=5 µm) (Interchim, Calif., USA) to get the pure product (23 mg; 23% yield). HPLC was then performed using a gradient elution with the mobile phase composed of an ammonium acetate buffer (20 mM) and ACN Elution was carried out at a flow rate of 21 mL/min for 10 min with the linear gradient from 10% to 100% of ACN, then the system was held at 100% of ACN with isocratic flow during 10 min. Temperature was set at 30° C. and UV detection was monitored at 280 nm and 257 nm. The retention time was 15 min, and the total yield of the pure product, after coupling and deprotection steps, corresponded to 9.5%.

IR, NMR and MS information of bioconjugate LENK-SQ-Diox: IR (neat, cm-1): v 3289, 2958, 2916, 2849, 1763, 1646, 1537, 1515, 1447, 1381, 1259, 1116, 1020, 982, 870, 802, 729, 700, 549, 493. 1H NMR (400 MHz, MeOD) δ: 7.31-7.23 (m, 4H, 2H Ar-ortho Phe, 2H Ar-meta Phe), 7.18 (m, 1H, H Ar-para Phe), 7.04 (d, 2H, H Ar-ortho Tyr, J=8.4 Hz), 6.71 (d, 2H, H Ar-meta Tyr, J=8.4 Hz), 5.77 (d, 1H, OCH2O, J=5.6 Hz), 5.71 (d, 1H, OCH2O, J=5.6 Hz), 5.19-5.04 (m, 5H, HC═C(CH3)), 4.65 (dd, 1H, CH Phe, J=4.9 Hz, J=9.6 Hz), 4.44 (m, 1H, CH Leu), 4.00-3.60 (m, 4H, 2 CH2 Gly), 3.54 (dd, 1H, CH Tyr, J=6.5 Hz, J=7.6 Hz), 3.16 (dd, 1H, C HaHb Phe, J=4.9 Hz, J=14.0 Hz), 3.10-2.87 (m, 2H, CHaHb Phe, CHaHb Tyr), 2.80 (dd, 1H, C HaHb Tyr, J=7.6 Hz, J=13.9 Hz), 2.44 (m, 2H, CH2-CH2CO SQ), 2.26 (m, 2H, CH2-CH2CO SQ), 2.14-1.90 (m, 16H, 8 CH2 SQ), 1.75-1.48 (m, 21H, CH2 Leu, CH(CH3)$_2$ Leu, 6 CH3 SQ), 0.94 (d, 3H, CH3 Leu, J=6.2 Hz), 0.90 (d, 3H, CH3 Leu, J=6.2 Hz). 13C NMR (75 MHz, MeOD) δ: 178.0 (CONH), 173.7 (CONH), 173.0 (CONH), 172.4 (CONH), 172.0 (CONH), 171.3 (CONH), 157.6 (C Ar-para Tyr), 138.3 (C Ar Phe), 136.0 (HC═C(CH3)), 135.8 (2 HC═C (CH3)), 134.1 (HC═C(CH3)), 132.0 (HC═C(CH3)), 131.5 (2CH Ar-ortho Tyr), 130.4 (2CH Ar-ortho Phe), 129.5 (2CH Ar-meta Phe, C Ar Tyr), 127.8 (CH Ar-para Phe), 126.5 (HC═C(CH3)), 125.7 (HC═C(CH3)), 125.5 (2 HC═C (CH3)), 125.4 (HC═C(CH3)), 116.5 (2CH Ar-meta Tyr), 80.9 (0-CH2-0), 62.6 (CH Tyr), 55.8 (CH Phe), 52.2 (CH Leu), 43.8 (CH2 Gly), 43.6 (CH2 Gly), 41.0 (CH2-CH (CH3)$_2$ Leu), 40.8 (CH2 SQ), 40.7 (2 CH2 SQ, CH2Tyr), 38.7 (CH2Phe), 35.3 (CH2-CH2-CO), 33.8 (CH2-CH2-CO), 30.7 (CH2 SQ), 30.4 (CH2 SQ), 29.2 (CH2 SQ), 27.8 (CH2 SQ), 27.5 (CH2 SQ), 25.9 (CH(CH3)$_2$ Leu), 23.4 (CH3 Leu), 21.9 (CH3 Leu), 17.8 (CH3 SQ), 16.7 (CH3 SQ), 16.2 (CH3 SQ), 16.1 (CH3 SQ), 16.0 (CH3 SQ), 14.5 (CH3 SQ). HRMS (+ESI): m/z 968.6064 ([M+H]+ calcd for C56H82N5O9: 968.6107).

Example 2: Synthesis of the Leu-enkephalin-squalene Bioconjugate with diglycolic Spacer (LENK-SQ-Dig)

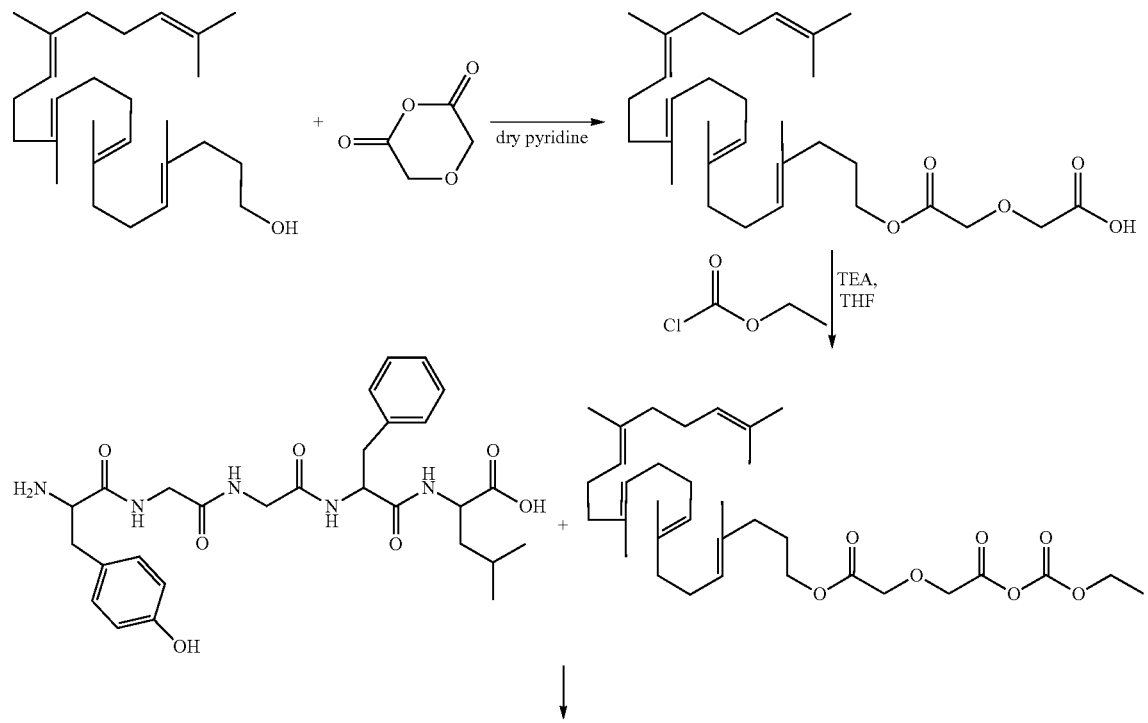

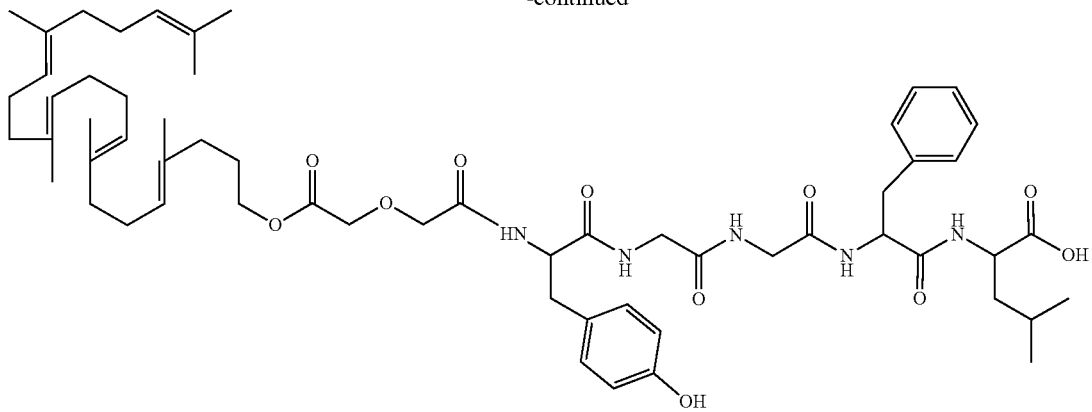

1,1',2-tris-norsqualenol was synthesized from squalene via 1,1',2-tris-norsqualenic aldehyde according to previously reported methods (35-37). To a solution of 1,1',2-tris-norsqualenol (200 mg, 0.52 mmol) in 3 mL of dry pyridine was added diglycolic anhydride (150 mg, 1.29 mmol). The reaction was stirred overnight at room temperature. The solvent was removed and the residue was extracted with DCM from dilute hydrochloric acid and brine. Conversion to the squalene-diglycolic acid, monitored by TLC, was approximately 100%. The resultant product was dried under vacuum, and used in the following step without further purification. To a solution of squalene-diglycolic acid (50 mg, 0.1 mmol) and triethylamine (TEA) (12 mg, 0.12 mmol) in 1 mL of anhydrous THF was added the ethyl chloroformate (10.8 mg, 0.1 mmol) under argon at 0° C. The reaction was stirred during 1 h at room temperature and a solution of LENK (55 mg, 0.1 mmol) in 1 mL anhydrous DMF was added. The mixture was maintained at 40° C. during 2 days with stirring under argon. The solvents were removed in vacuo and the crude product was purified using silica gel chromatography (purified with gradient eluent DCM/EtOH: 100/0 to 90/10).

Then ammonium salt was eliminated by simple filtration on silica using EtOH/AcOEt (40/60) as solvents. The pure bioconjugate was obtained with 69% of yield.

IR, NMR and MS information of bioconjugate LENK-SQ-Dig: IR (neat, cm-1): v 3297, 3068, 2958, 2924, 2851, 1653, 1516, 1443, 1260, 1142, 1099, 1020, 799, 699, 583. 1H NMR (400 MHz, MeOD) δ: 7.30-7.22 (m, 4H, 2H Ar-ortho Phe, 2H Ar-meta Phe), 7.19 (m, 1H, H Ar-para Phe), 7.06 (d, 2H, H Ar-ortho Tyr, J=8.5 Hz), 6.71 (d, 2H, H Ar-meta Tyr, J=8.5 Hz), 5.20-5.05 (m, 5H, HC=C(CH3)), 4.65 (dd, 1H, CH Phe, J=4.7 Hz, J=9.4 Hz), 4.57 (dd, 1H, CH Tyr, J=6.1 Hz, J=8.3 Hz), 4,40 (m, 1H, CH Leu), 4.17-3.85 (m, 6H, 2 C H2 Diglycolyl, C H2-O SQ), 3.90-3.72 (m, 4H, 2 C H2 Gly), 3.20 (dd, 1H, C HaHb Phe, J=4.7 Hz, J=14.0 Hz), 3.11 (dd, 1H, C HaHb Tyr, J=6.1 Hz, J=13.9 Hz), 3.00-2.89 (m, 2H, CHaHb Phe, CHaHb Tyr), 2.14-1.93 (m, 19H, 9 CH2 SQ, CHaHb-CH2-O SQ), 1.74 (m, 1H, CHaHb-CH2-O SQ), 1.71-1.54 (m, 21H, CH2 Leu, CH(CH3)2, 6 CH3 SQ), 0.94 (d, 3H, CH3 Leu, J=6.2 Hz), 0.91 (d, 3H, CH3 Leu, J=6.2 Hz). 13C NMR (75 MHz, MeOD) δ: 176.8 (CONH), 174.2 (CONH), 173.4 (CONH), 172.2 (O—CO—CH2), 172.0 (CONH), 171.3 (CONH), 157.5 (C Ar-para Tyr), 138.5 (C Ar Phe), 135.9 (3 HC=C (CH3)), 134.8 (HC=C(CH3)), 132.0 (HC=C(CH3)), 131.4 (2CH Ar-ortho Tyr), 130.4 (2CH Ar-ortho Phe), 129.4 (2CH Ar-meta Phe), 128.6 (C Ar Tyr), 127.7 (CH Ar-para Phe), 126.3 (HC=C(CH3)), 125.6 (2 HC=C(CH3)), 125.5 (HC=C(CH3)), 125.4 (HC=C(CH3)), 116.3 (2CH Ar-meta Tyr), 71.5 (0-CH2-0), 69.4 (CO—CH2-O), 65.9 (CH2-CH2-CH2-O), 56.2 (CH Tyr), 56.0 (CH Phe), 52.3 (CH Leu), 44.0 (CH2 Gly), 43.4 (CH2 Gly), 41.7 (CH2-CH(CH3)2 Leu), 38.6 (CH2Phe), 37.9 (CH2 Tyr), 36.8 (CH2-CH2-CH2-O), 29.2 (CH2 SQ), 27.8 (2 CH2 SQ), 27.6 (3 CH2 SQ), 25.9 (CH(CH3)2 Leu, CH3 SQ), 23.4 (CH3 Leu), 22.0 (CH3 Leu), 17.8 (CH3 SQ), 16.2 (2 CH3 SQ), 16.0 (2 CH3 SQ). HRMS (–ESI): m/z 1038.61572 ([M–H]– calcd for C59H84N5O11: 1038.61618).

Example 3: Synthesis of the Leu-enkephalin-squalene Bioconjugate with Amide Spacer (LENK-SQ-Am)

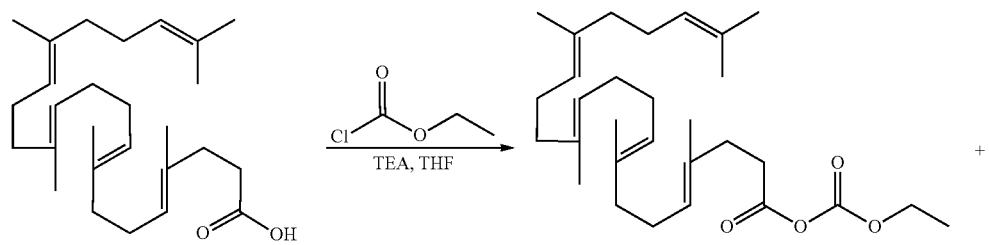

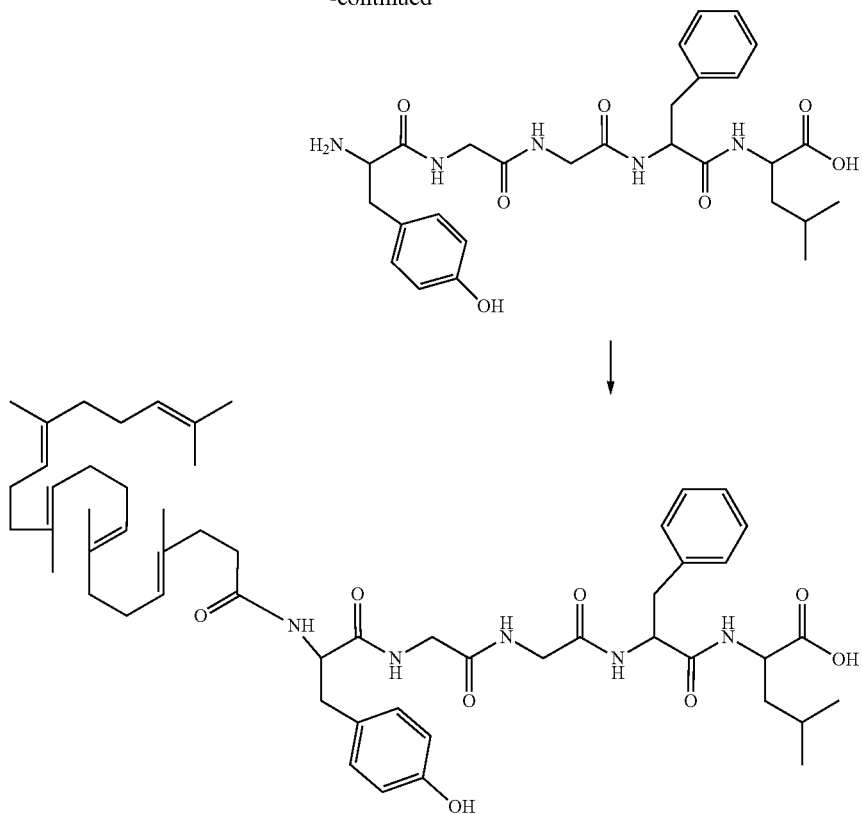

1,1',2-Tris-nor-squalenic acid (100 mg, 0.25 mmol) and TEA (34.79 mg, 0.3 mmol) were dissolved in 1.5 mL of anhydrous THF under argon and ethyl chloroformate (27 mg, 0.25 mmol) was added to the mixture at 0° C. The reaction was allowed to warm at room temperature and kept under stirring for 1 h. A solution of LENK (138 mg, 0.25 mmol) in 1.5 mL of anhydrous DMF was then added to the reaction and the mixture was kept under stirring for 2 days. The solvents were removed in vacuo and the crude product was purified twice using silica gel chromatography (purification with gradient eluent DCM/EtOH: 100/0 to 90/10 and then simple filtration with EtOH/AcOEt: 40/60 to remove the ammonium salt). The pure bioconjugate was obtained with 73% of yield.

IR, NMR and MS information of bioconjugate LENK-SQ-Am: IR (neat, cm-1): v 3303, 2957, 2925, 2856, 1711, 1697, 1543, 1516, 1440, 1282, 1241, 1213, 828, 671. 1H NMR (400 MHz, MeOD) δ: 7.31-7.22 (m, 4H, 2H Ar-ortho Phe, 2H Ar-meta Phe), 7.18 (m, 1H, H Ar-para Phe), 7.05 (d, 2H, H Ar-ortho Tyr, J=8.5 Hz), 6.71 (d, 2H, H Ar-meta Tyr, J=8.5 Hz), 5.19-5.05 (m, 5H, HC=C(CH3)), 4.68 (dd, 1H, CH Phe, J=4.9 Hz, J=9.2 Hz), 4.50-4.39 (m, 2H, CH Tyr, CH Leu), 3.87-3.67 (m, 4H, 2 CH2 Gly), 3.20 (dd, 1H, C HaHb Phe, J=4.9 Hz, J=14.0 Hz), 3.07-2.93 (m, 2H, CHaHb Phe, CHaHb Tyr), 2.85 (dd, 1H, C HaHb Tyr, J=8.2 Hz, J=13.8 Hz), 2.31 (m, 2H, CH2-CH2-CO) 2.18 (m, 2H, CH2-CH2-CO), 2.13-1.88 (m, 16H, 8 CH2 SQ), 1.73-1.53 (m, 21H, CH2 Leu, CH(CH3)2 Leu, 6 CH3 SQ), 0.94 (d, 3H, CH3 Leu, J=6.2 Hz), 0.91 (d, 3H, CH3 Leu, J=6.2 Hz). 13C NMR (75 MHz, MeOD) δ: 176.2 (CO2H), 175.8 (CONH), 174.7 (CONH), 173.3 (CONH), 172.0 (CONH), 171.2 (CONH), 157.4 (C Ar-para Tyr), 138.4 (C Ar Phe), 136.0 (2 HC=C(CH3)), 135.8 (HC=C(CH3)), 134.7 (HC=C(CH3)), 132.0 (HC=C(CH3)), 131.3 (2CH Ar-ortho Tyr), 130.4 (2CH Ar-ortho Phe), 129.4 (2CH Ar-meta Phe), 128.9 (C Ar Tyr), 127.7 (CH Ar-para Phe), 126.2 (HC=C(CH3)), 125.6 (HC=C(CH3)), 125.5 (HC=C(CH3)), 125.5 (2 HC=C(CH3)), 116.3 (2CH Ar-meta Tyr), 56.9 (CH Tyr), 55.9 (CH Phe), 52.3 (CH Leu), 43.9 (CH2 Gly), 43.3 (CH2 Gly), 41.7 (CH2-CH(CH3)2 Leu), 38.7 (CH2Phe), 37.9 (CH2 Tyr), 36.5 (CH2-CH2-CO), 35.8 (CH2-CH2-CO), 29.2 (3 CH2 SQ), 27.8 (4 CH2 SQ), 27.5 (2 CH2 SQ), 25.9 (CH(CH3)2 Leu, CH3 SQ), 23.4 (CH3 Leu), 21.9 (CH3 Leu), 17.7 (CH3 SQ), 16.2 (2 CH3 SQ), 16.1 (CH3 SQ), 16.0 (CH3 SQ). HRMS (−ESI): m/z 936.5826 ([M−H]− calcd for C55H78N5O8: 936.5845).

Example 4: Preparation of Nanoparticles (LENK-SQ-NP)

A. Preparation of Nanoparticles (LENK-SQ-NP)

LENK-SQ NPs were prepared using the nanoprecipitation methodology. Briefly, the LENK-SQ bioconjugate (ie. LENK-SQ-Diox, LENK-SQ-Dig or LENK-SQ-Am) was dissolved in EtOH (8 mg/mL) and added dropwise under stirring (500 rpm) into a 5% aqueous dextrose solution (volume ratio EtOH: dextrose solution=1:4). The solution became spontaneously turbid with a tyndall effect, indicating the formation of the nanoparticles. Ethanol was then completely evaporated using a Rotavapor® (80 rpm, 30° C., 30 mbar) to obtain an aqueous suspension of pure LENK-SQ NPs (final concentration 2 mg/mL). Blank SQ NPs (LENK-free NPs) were prepared by the same method as described above by adding dropwise an ethanolic solution of squalenic acid into 5% aqueous dextrose solution. Fluorescent LENK-SQ NPs were also obtained by the same procedure, except that the fluorescent probe DiD was solubilized in the ethanolic phase together with the LENK-SQ-Am bioconjugate (ratio DiD:LENK-SQ-Am was 4% wt/wt), before addition to the dextrose solution. The peptide drug loadings into the NPs were expressed as percentage (%), calculated from the ratio between LENK peptide Mw and LENK-SQ bioconjugate Mw. The LENK-SQ nanoparticles were regularly observed by cryo-TEM. All the NPs were freshly prepared and used within 2 h (conservation at 4° C.) before in vivo experiments.

B. Characterization of LENK-SQ Nanoparticles

1. Dynamic Light Scattering (DLS) Measurement.

The mean particle size, polydispersity index (PDI) and zeta potential were primarily evaluated by DLS (Nano ZS, Malvern; 173° scattering angle at 25° C.).

The measurements were performed in triplicate following appropriate dilution of the nanoparticles in water (DLS) or in 0.1 mM KCl (zeta potential).

2. Cryo-TEM.

The morphology of the LENK-SQ NPs was investigated by Cryo-TEM. NPs were vitrified using a chamber designed and set up in the laboratory where both humidity and temperature could be controlled. 4 µL solution of LENK-SQ NPs (4 mg/mL in Milli-Q water) was deposited onto a perforated carbon film mounted on a 200 mesh electron microscopy grid. The homemade carbon film holes dimensions were about 2 mm in diameter. Most of the drop was removed with a blotting filter paper and the residual thin films remaining within the holes were quick-frozen by plunging them in liquid ethane cooled with liquid N2. The specimen was then transferred, using liquid N2, to a cryo-specimen holder and observed using a JEOL FEG-2010 electron microscope. Micrographs were recorded at 200 kV under low-dose conditions at a magnification of 40 000 on SO-163 Kodak films. Micrographs were digitized using a film scanner (Super coolscan 8000 ED, Nikon), and analysis was made using the ImageJ software.

3. Results Results are shown in FIG. 1.

All bioconjugates showed the capability to self-assemble as NPs in aqueous solution after nanoprecipitation from LENK-SQ ethanolic solutions.

When measured by DLS, the size of the NPs varied from 60 to 120 nm, depending on the linkage between squalene and enkephalin (see FIG. 1). The difference in NPs zeta potential was related to the nature of the exposed amino acids onto the NPs surface. Indeed, in case of the LENK-SQ-Diox bioconjugate, the squalene conjugation on the C-terminus LENK peptide let its N-terminus site free (primary amino group), leading to a net positive charge. On the contrary, the zeta potential became negative when the conjugation with SQ was performed on the N-terminus LENK peptide (LENK-SQ-Dig and LENK-SQ-Am). Drug loadings (see FIG. 1) ranged between 53% and 60% which was much higher than in conventional nanoparticles or liposomes which amounted to a maximum of 5% (23).

All bioconjugates displayed spherical and monodisperse structures with sizes ranging from 50 nm to 100 nm. The slight discrepancy between DLS and Cryo-TEM size measurements could be attributed to the known hydrodynamic radius-related differences.

Example 5: In Vitro LENK Release from LENK-SQ Nanoparticles in Serum

A. Material and Method

Frozen serum of male SWISS mice (900 µL) was quickly thawed and then pre-incubated at 37° C. for 30 min before the addition of 300 µL LENK-SQ-Dig NPs or LENK-SQ-Am NPs (2 mg/mL). In the case of LENK-SQ-Diox NPs, diluted serum (30% in 5% dextrose solution) was used for the release study. At various time intervals, aliquots (80 µL) were collected and added into 320 µL ACN to denature and precipitate the enzymes and proteins of the serum, in order to remove them after centrifugation (3000 rcf for 15 min). To quantify the residual LENK-SQ bioconjugate and the released LENK, the resulting supernatants (150 µL) were evaporated to dryness at 40° C. under nitrogen flow, and then solubilized in 150 µL of Milli-Q water. Free peptide quantification was performed using RP-HPLC on a Uptisphere Strategy C18HQ column (4.6×100 mm, 5 µm, Interchim), a 1525 Binary LC Pump (Waters, a 2707 Auto-sampler (Waters) and a 2998 PDA detector (Waters). The HPLC was carried out using a gradient elution with the mobile phase composed of 5 mM ammonium acetate in milli-Q water (phase A) and 5 mM ammonium acetate in ACN (phase B). Elution was carried out at a flow rate of 1 mL/min for 13 min with the linear gradient from 10% to 100% of B; then, the system was held at 100% of B with isocratic flow during 10 min. Temperature was set at 35° C. and UV detection was monitored at 257 nm.

B. Results

Figure 2:
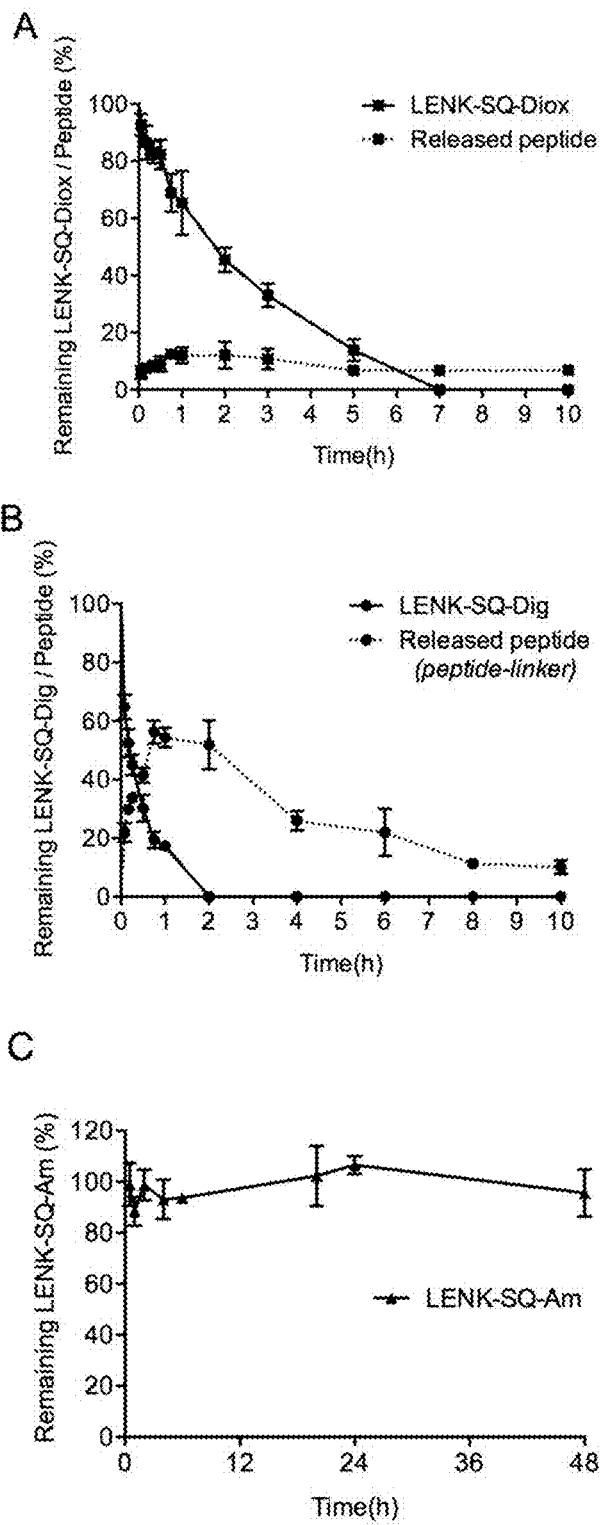
FIG. 2 shows in vitro bioconversion of LENK-SQ bioconjugates into LENK in the presence of serum. (A) LENK-SQ with dioxycarbonyl linker (B) LENK-SQ with diglycolic linker (C) LENK-SQ with amide bond. Solid lines and dashed lines represent the bioconjugates and the released peptides, respectively.

Results are shown in FIG. 2.

The incubation of LENK-SQ-Diox in serum resulted in a decrease of the bioconjugate, which correlated well with the release of the peptide (see FIG. 2A). The concentration of the bioconjugate decreased gradually till 7 h, while LENK-SQ-Diox NPs progressively released the free LENK peptide. The peptide was then slowly degraded by the peptidases of the serum but still lasted beyond 10 h post-incubation (See FIG. 2A). The incubation of LENK-SQ-Dig in serum resulted in a decrease of the bioconjugate until completely disappearance at 2 h, but no presence of free peptide was detected. The RP-HPLC analyses, however, highlighted a slow release of the peptide still attached to its linker. This release reached a maximum at 45 min followed by progressive degradation of the peptide-linker fragment which could still be detected over 10 h (See FIG. 2B). On the contrary, LENK-SQ-Am remained stable in serum, without significant decrease during 48 h, and no peptide was released in the course of the experiment (See FIG. 2C).

Example 6: Analgesic Efficacy of LENK-SQ-NPs

A. Material and Method

1. Animals:

Adult male Sprague-Dawley rats (200-220 g on arrival, 280-300 g at the time of experiments) and adult male Swiss mice (18-20 g on arrival, 22-25 g at the time of experiments) were purchased from Janvier Labs (France) for algesimetry tests and biodistribution respectively. They were housed in a standard controlled environment (22±1° C., 60% relative humidity, 12:12 h light-dark cycle, lights on at 8:00 a.m.) with food and water available ad libitum, without any handling for at least 1 week before being used for experiments.

2. Carrageenan-Induced Hind Paw Inflammation

λ-Carrageenan was dissolved in physiological saline (NaCl, 0.9%) just prior to injection. Rats or mice received a single intraplantar injection of λ-carrageenan solution in the plantar region of the right hind paw (25, 39) in order to induce inflammation. The injected λ-carrageenan dose corresponded to 100 µL (2% solution w/v) for rat, and 20 µL (3% solution w/v) for mice. Inflammation reached its maximum 3 h after λ-carrageenan injection. Thermal nociceptive test was then performed on the ipsilateral inflamed hind paw.

3. Nociceptive Behavioral Study in Rats a. Thermal Nociceptive test

Hypersensitivity to thermal nociceptive stimuli was assessed using the Hargreaves test (25). Rats were placed individually in an open Plexiglas cylindrical chamber (20 cm in diameter, 35 cm high) on a 3 mm thick transparent glass floor, and allowed to habituate for at least 20 min before testing. A moveable radiant heat source (Model 7370, Ugo Basile plantar test, Italy) was positioned under the glass floor directly beneath the plantar surface of the right hind paw and the time (in seconds) that elapsed from switching on the radiant heat until paw withdrawal was measured automatically. A cut-off time of 20 s was established to prevent tissue damage. Each trial was repeated 3 times with 5 min intervals for basal threshold and 2 times spaced of 2 min after NPs treatments at 3 h after λ-carrageenan injection. The average of paw withdrawal latencies (PWL) was calculated and expressed as mean values ±SEM. (standard error of mean).

b. Experimental Design for Algesimetry Test

Basal responses to thermal stimuli were obtained on the day before the λ-carrageenan injection. On the basis of previous studies, acute pharmacological treatments were performed 3 h post-carrageenan injection, which corresponded to the peak inflammatory response.

Figure 3:
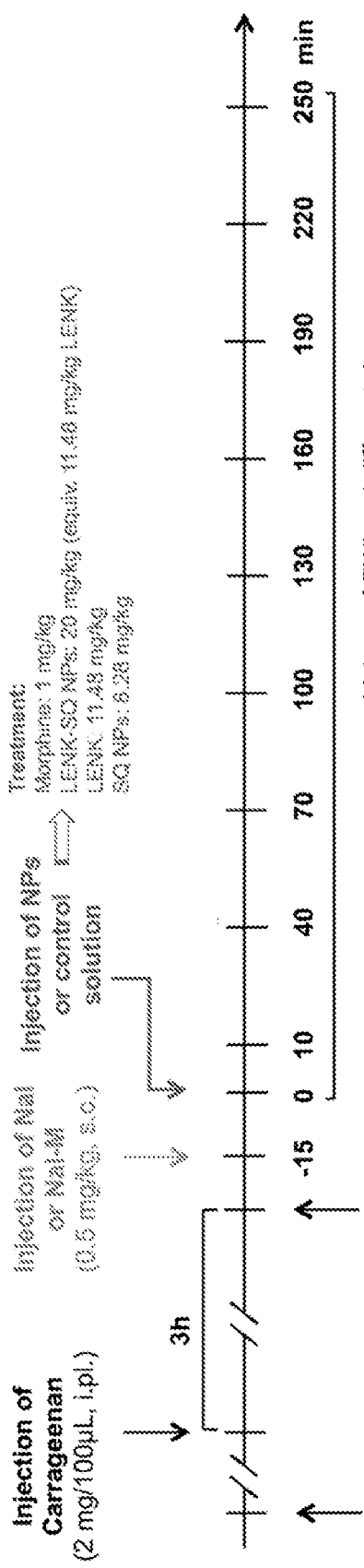
FIG. 3 discloses to the experimental design for algesimetry. The antinociceptive effect of NPs was tested in a pathophysiological context induced by an intraplantar carrageenan injection (2% in saline, 100 μL). Involvement of central or peripheral opioid receptors was performed using a brain-permeant opioid antagonist naloxone (NaI) and a brain-impermeant opioid receptor antagonist naloxone methiodide (NaI-M). NPs suspensions or control solutions were injected intravenously with a dose volume of 10 mL/kg during 30 s. Hargreaves test was performed 10 min after NPs administration and then every 30 min till 250 min. The dose of LENK-SQ NPs 20 mg/kg was equiv. to 11.48 mg/kg LENK and to 8.28 mg/kg SQ NPs, and corresponded to 20.66 mmol/kg for both LENK-SQ and LENK.

The efficacy of these treatments on thermal hyperalgesia was evaluated by measurement of paw withdrawal latencies (PWL) using Hargreaves test at regular time intervals after drug or vehicle administration, first at 10 min and then each 30 min during a period of 4 h (FIG. 3).

c. Acute Pharmacological Treatments

Morphine and LENK were dissolved in dextrose 5%, whereas NaI and NaI-M were dissolved in physiological saline (NaCl, 0.9%). All these drugs and NPs suspensions were prepared just before administration. All acute treatments were performed at 3 h after λ-carrageenan intraplantar injection according to FIG. 3. NaI and NaI-M were injected subcutaneously (s.c.) whereas the intravenous (i.v.) route in the tail vein was used for LENK-SQ NPs, LENK and their controls. The antagonist (NaI or NaI-M) was administered 15 min before the agonist (morphine or tested NPs). A single dose of morphine (1 mg/kg), NaI (0.5 mg/kg) and NaI-M (0.5 mg/kg) was administered based on literature data (40). A single i.v. dose of LENK-SQ NPs (20 mg/kg, equivalent to 11.48 mg/kg of LENK) or control unconjugated SQ NPs (8.28 mg/kg) was used, based on maximal volume of LENK-SQ NPs that could be injected.

Figure 4:
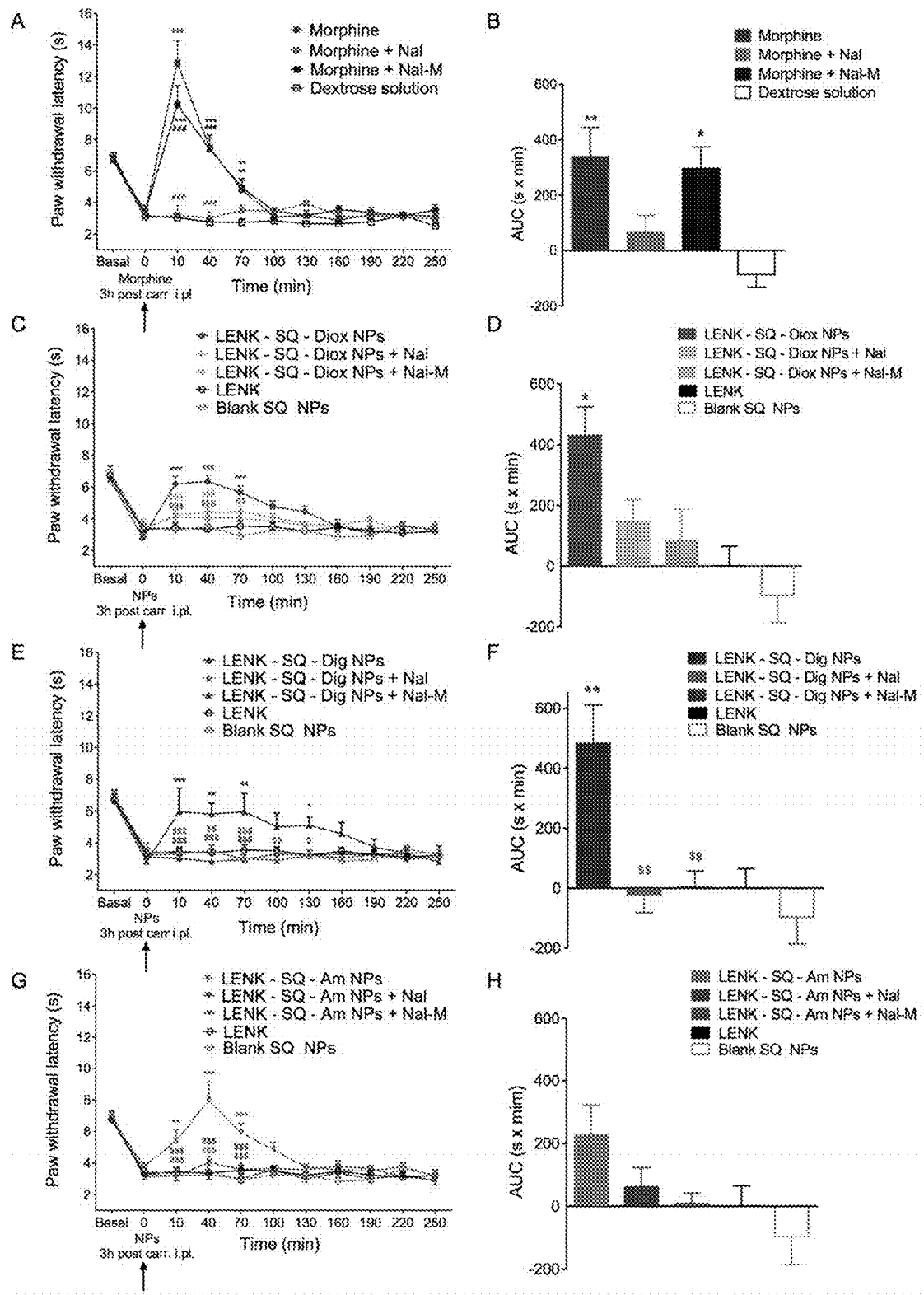
FIG. 4 shows anti-hyperalgesic effects of acute treatment with Morphine (A, B), LENK-SQ-Diox NPs (C, D), LENK-SQ-Dig NPs (E, F) and LENK-SQ-Am NPs (G, H) in λ-carrageenan-induced inflammatory pain injected rats. Administration of morphine, LENK-SQ NPs, NaI, NaI-M, LENK, blank SQ NPs or dextrose solution (vehicle) was performed (arrow, 0 on abscissa) 3 h after λ-carrageenan injection into the right hind paw. Morphine (A), LENK-SQ-Diox NPs (C), LENK-SQ-Dig NPs (E) and LENK-SQ-Am NPs (G) induced an increase in paw withdrawal latency (in seconds, mean±SEM of independent determinations in 5-9 animals per group) in the Hargreaves test. *, #, $ P<0.05, , ##, $$ P<0.01, *, ###, $$$ P<0.001 (*: compared to dextrose solution or LENK solution, #: compared to morphine; $: compared to LENK-SQ NPs. Two-way Anova with repeated measures, Bonferroni post test). NaI or NaI-M was administered 15 min prior to morphine or LENK-SQ NPs injection. Basal on abscissa: control (naïve) rats (prior to λ-carrageenan injection). B, D, F and H: Bars are the mean±SEM of AUCs (second×minute) of the cumulative durations derived from the time course changes (A, C, E and G) in paw withdrawal latency after the various treatments. *, $ P<0.05, , $$ P<0.01, *, $$$ P<0.001, one way Anova, Tukey post test, *: compared to dextrose (vehicle) or LENK solution, $: compared with LENK-SQ NPs.

Results are shown in FIG. 4.

B. Effect of Intraplantar λ-Carrageenan Injection on Thermal Sensitivity

Intraplantar injection of λ-carrageenan into the right hind paw induced a local inflammatory response characterized by marked edema, hyperthermia, and hyperalgesia restricted to the injected right hind paw. Thermal hypersensitivity was developed in all the rats with a mean decrease of 52.48% of PWL compared to the basal PWLs in naïve rats. (P<0.001; see FIG. 4).

C. Effect of Morphine on Thermal Sensitivity

The acute treatment with 1 mg/kg morphine (FIG. 4A) reduced the thermal hyperalgesia as shown by the resulting significant increase in PWLs. Indeed, 10 min post-morphine injection, the PWL reached 12.87±1.38 s, while it remained at 3.05±0.20 s after treatment with a control dextrose solution (FIG. 4A). However, morphine anti-hyperalgesic pharmacological activity disappeared rapidly and no longer significant effect was observed as soon as 100 min post-morphine administration (FIG. 4A).

D. Effect of LENK-SQ-NPs on Thermal Sensitivity

The antihyperalgesic effect of LENK-SQ NPs with the 3 different linkers was evaluated during 4 h after their administration (FIG. 4C-H). All injected rats with LENK-SQ NPs displayed significant reduction of thermal hyperalgesia, as expressed by a dramatic increase of respective AUC values in comparison with λ-carrageenan-treated rats injected with either the free LENK peptide or the blank SQ NPs (FIG. 4D, F, H). In particular, the anti-hyperalgesic activity was significant at all time points from 10 min to 130 min in rats injected with LENK-SQ Diox NPs or LENK-SQ Am NPs (FIG. 4C, G). As shown in FIG. 4E, LENK-SQ-dig NPs also displayed a significant anti-hyperalgesic effect, with a maximum increase in PWL maintained from 10 min to 130 min post-injection, and a progressive decline down to baseline at 220 min.

Interestingly, maximal PWL values reached after administration of LENK-SQ NPs in λ-carrageenan-treated rats corresponded to basal PWL values measured in control naïve rats, before λ-carrageenan treatment (FIG. 4C, E, G), indicating a pure anti-hyperalgesic action of these nanoparticles. In contrast, morphine injection in λ-carrageenan-treated rats resulted in PWL values twice as high as those found in control naïve rats (FIG. 4A), as expected of not only an anti-hyperalgesic effect but also the well-established analgesic effect of the opiate agonist.

In addition, blank SQ NPs (without the LENK) did not demonstrate any anti-hyperalgesic activity (FIG. 4), which indicated that the analgesic response to LENK-SQ NPs administration resulted from the release of LENK peptide.

E. Effects of Opioid Receptor Blockade Using Naloxone and Naloxone Methiodide

In order to ascertain the involvement of central or peripheral opioid receptors during the anti-hyperalgesic effect of LENK-SQ NPs, naloxone (NaI, brain-permeant opioid receptor antagonist) or naloxone methiodide (NaI-M, brain-impermeant opioid receptor antagonist) (26) were subcutaneously injected 15 min prior to the injection of morphine or NPs (FIG. 3).

F. Effects of Opioid Receptor Antagonists on Morphine-Induced Anti-Hyperalgesic Effect Pre-administration of the non-selective opioid receptor antagonist NaI (0.5 mg/kg s.c.) abolished the amplitude and the duration of the anti-hyperalgesic effect of morphine (PWL 3.20±0.59 s vs 12.87±1.38 s at 10 min) and decreased the corresponding AUC value by 81% in comparison with the morphine group (FIG. 4B). The peripheral opioid receptor antagonist, NaI-M, was markedly less effective since it reduced the morphine's effect by only 13%. (FIG. 4A and FIG. 4B).

G. Effects of Opioid Receptor Antagonists on LENK-SQ NPs-Induced Anti-Hyperalgesic Effect Pre-administration of either NaI or its quaternary derivative NaI-M, abrogated the anti-hyperalgesic effect of the three LENK-SQ NPs (FIG. 4C-H). Indeed, NaI pre-treatment caused a reduction of 66%, 105% or 73% of the AUC values compared to these found in rats injected with LENK-SQ-Diox, LENK-SQ-Dig and LENK-SQ-Am NPs alone, respectively. The corresponding reductions in AUC values with NaI-M reached 81%, 99% and 96%, respectively, indicating that the selective blockade of peripheral opioid receptors only was enough to abrogate the anti-hyperalgesic effects of LENK-SQ NPs.

Example 7: Biodistribution of LENK-SQ NPs

A. Biodistribution Studies in Mice

In vivo imaging biodistribution studies were performed after i.v. injection of fluorescent LENK-SQ-Am NPs (250 µL, 2 mg/mL containing 4% DiD) or control fluorescent DiD solution (250 µL, 80 µg/mL in 5% dextrose solution) in shaved mice bearing λ-carrageenan-induced inflammation. In parallel, control non-inflamed shaved mice (injected with 20 µL saline into the right hind paw, instead of λ-carrageenan), received also injection of fluorescent LENK-SQ NPs. The biodistribution of the NPs was recorded at 0.5, 2, 4, 6 and 24 h after excitation at 640 nm and emission in the 695-775 nm filter respectively, using IVIS Lumina LT series III system (Caliper, Life science). During imaging, the mice were kept on the imaging stage under anesthesia with 2% isoflurane gas in oxygen flow (1 L/min) and were imaged in ventral position. Images and measures of fluorescence signals were acquired and analyzed with Living Imaging®. To measure photon radiance, regions of interest (ROI, threshold of 35%) were selected on the paw of the mice and average radiant efficiency values were used for quantification. Threshold of ROI for the inflamed paw was then pasted on the non-inflamed paw to compare the radiance with the same region.

In a separate experiment, fluorescent LENK-SQ NPs injected mice were deeply anesthetized with a mixture of ketamine (100 mg/kg, i.p.) and xylazine (10 mg/kg, i.p.) before euthanisia by transcardiac perfusion of 40 ml saline (8 mL/min), until the fluid exiting the right atrium was entirely clear. Then, liver, spleen, kidneys, heart, lungs, brain, and inflamed right hind paw were excised and immediately imaged with the imager. The fluorescence emitted was quantified with Living Image software over the ROI (threshold of 20%).

B. Results

Figure 5:
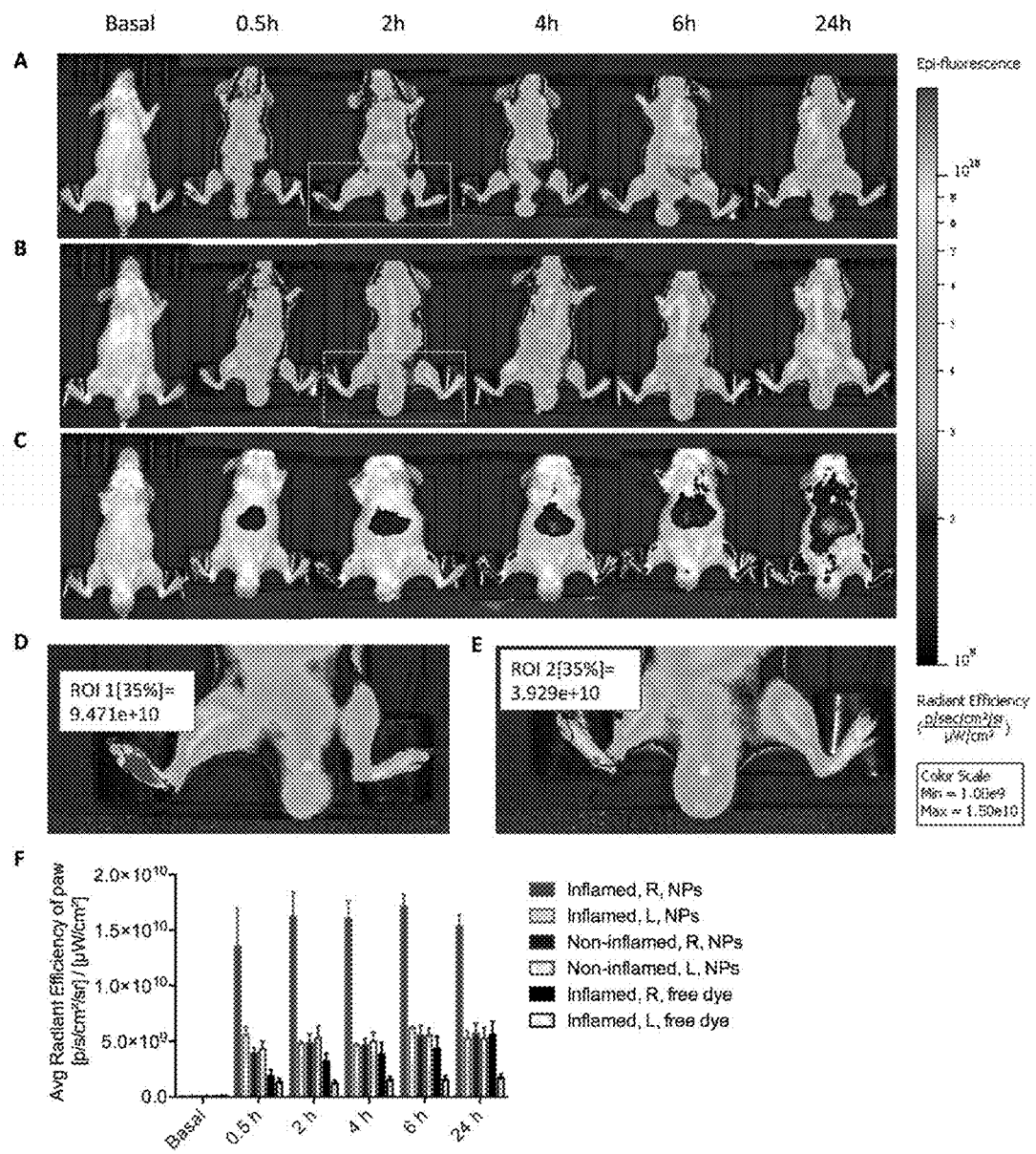
FIG. 5 shows lumina scan of mice and of their organs after intravenous administration of fluorescent LENK-SQ-Am NPs or control fluorescent dye solution (ventral view). (A) Biodistribution of fluorescent LENK-SQ-Am NPs in mice with inflamed right hind paw. (B) Biodistribution of fluorescent LENK-SQ-Am NPs in mice with non-inflamed hind paw (saline only injected into the right hind paw). (C) Biodistribution of free dye in mice with inflamed right paw. (D) Zoom of group A at 2 h. (E) Zoom of group B at 2 h. (F) Quantitative analysis of the paws with the same region of interest (ROI). R=right hind paw and L=left hind paw.

The in vivo biodistribution of LENK-SQ-Am NPs was assessed after intravenous injection of DiD-fluorescently labeled LENK-SQ-Am NPs in a murine λ-carrageenan-induced paw edema model (right hind paw). The fluorescence in tissues was monitored up to 24 h, non-invasively, from the abdomen side using an IVIS Lumina (FIG. 5). Mice injected with saline into the paw were used as non-inflamed control. The real-time in vivo imaging showed, in comparison with the healthy paw, an increase by 2-3 times of the average radiant efficiency within the inflamed paw after iv injection of fluorescent LENK-SQ-Am NPs (FIG. 5A, D, F). In a control experiment, when the λ-carrageenan administered mice were intravenously injected with a single DiD solution, no significant accumulation of fluorescence was observed in the inflamed paw (FIG. 5C, F). In another control experiment, mice were injected locally with saline at the hind paw and intravenously treated with fluorescent LENK-SQ NPs. No significant accumulation of fluorescence at hind paw level was also observed under this condition (FIG. 5B, E) showing that the accumulation of fluorescence in the λ-carrageenan-inflamed paw was not due to the local hind paw injection per se.

Figure 6:
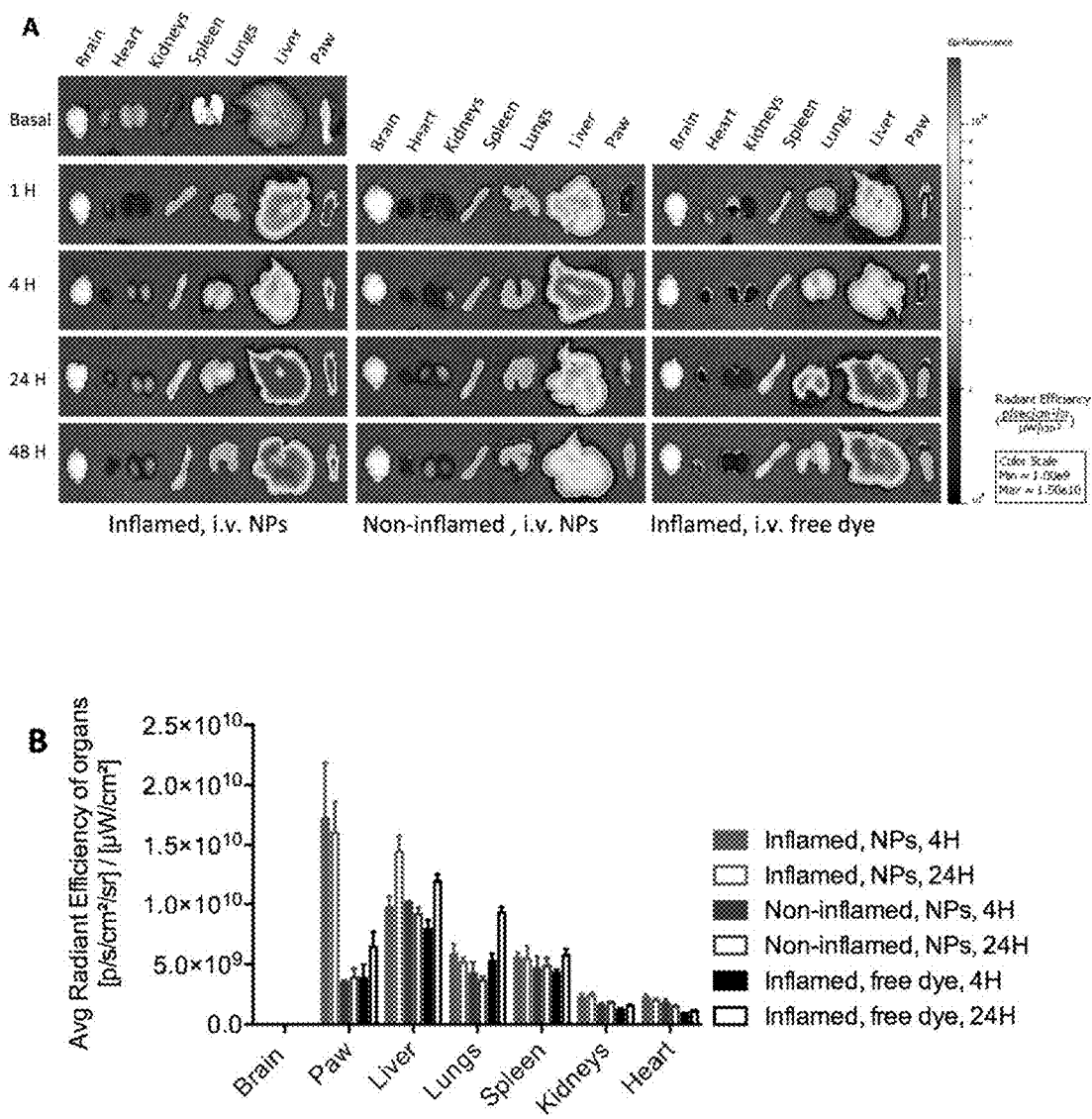
FIG. 6 shows the biodistribution of fluorescent LENK-SQ-Am NPs or control fluorescent dye solution in mice with or without inflamed paw. 4 h after λ-carrageenan or saline injection into the right paw, fluorescent LENK-SQ NPs or free dye were intravenously introduced into the mice. At different time points, mice were deeply anesthetized with a mixture of ketamine (100 mg/kg, i.p.) and xylazine (10 mg/kg, i.p.) before euthanasia by transcardiac perfusion of 40 ml saline (8 mL/min), until the fluid exiting the right atrium was entirely clear. Then, liver, spleen, kidneys, heart, lungs, brain, and inflamed right hind paw were excised and immediately imaged with the imager. The fluorescence emitted was quantified with Living Image software over the region of interest (ROI) with the threshold of 20%. (A) Ex vivo fluorescence imaging of the harvested brain, heart, kidneys, lung, liver and paw from fluorescent NPs or free dye-injected SWISS mice. (B) Average radiant efficiency of these organs after 4 or 24 h injection of NPs or free dye.

Finally, in a separate experiment, 4 h after the intravenous injection of fluorescent NPs or DiD solution, animals were euthanized and transcardially perfused with 40 mL of saline to remove the fluorescence from the blood. After collection of tissues, a strong ex vivo fluorescence signal was again observed in the inflamed paw, but also in the liver, the spleen and the lungs, whereas no detectable accumulation of fluorescence occurred in the brain of the animals (FIG. 6).

The invention claimed is:

1. A bioconjugate comprising at least one neuropeptide covalently bond to at least one hydrocarbon compound of squalene structure (SQ), as represented as follows,

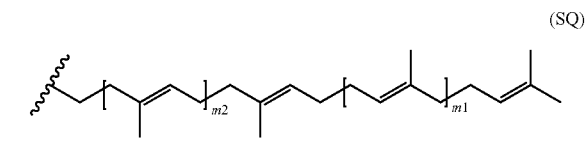

wherein:
m1 is 0,1,2,3,4,5,6,7,8, or 9, and
m2 is 0,1,2,3,4,5,6,7,8, or 9,
and wherein

represents the bond to the at least one neuropeptide, and
wherein the at least one neuropeptide has a C-terminal acid covalently bonded to the at least one hydrocarbon compound of squalene structure by using a dioxycarbonyl spacer or the at least one neuropeptide has a N-terminal amine covalently bonded to the at least one hydrocarbon compound of squalene structure by using a diglycolate spacer.

2. The bioconjugate according to claim 1, wherein the at least one hydrocarbon compound of squalene structure comprises from 11 to 102 carbon atoms.

3. The bioconjugate according to claim 1, wherein the at least one hydrocarbon-based of squalene structure able to form said bioconjugate is squalenic acid or a squalenic acid derivative, wherein the squalenic acid derivative is selected from the group consisting of 1,1',2-tris-nor-squalenic acid, 1,1',2-tris-nor-squalenol, 1,1',2-tris-nor-squalenethiol, squalene acetic acid, squalenylethanol, and squalenylethanethiol.

4. The bioconjugate according to claim 1, wherein the at least one neuropeptide is an opioid peptide.

5. The bioconjugate according to claim 4, wherein the opioid peptide is leucine enkephalin (LENK).

6. The bioconjugate according to claim 4, wherein the opioid peptide is selected from the group consisting of methionine enkephalin (MENK), dalargin, kyotorphin, endomorphins, endorphins and a derivative thereof.

7. The bioconjugate according to claim 1, wherein the at least one neuropeptide has a N-terminal amine covalently bonded to the at least one hydrocarbon compound of squalene structure by using a diglycolate spacer and the at least one hydrocarbon compound of squalene structure is derived from the molecule of 1,1',2-tris-nor-squalenol.

8. The bioconjugate according to claim 1, wherein the at least one neuropeptide has a C-terminal acid covalently bonded to the at least one hydrocarbon compound of squalene structure by using a dioxycarbonyl spacer and the at least one hydrocarbon compound of squalene structure is derived from the molecule of 1,1',2-tris-nor-squalenic acid.

9. The bioconjugate according to claim 1, wherein the bioconjugate is

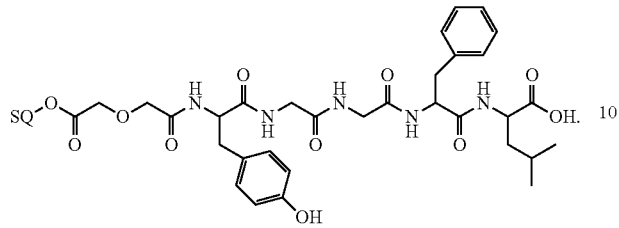

10. The bioconjugate according to claim 1, wherein the bioconjugate is:

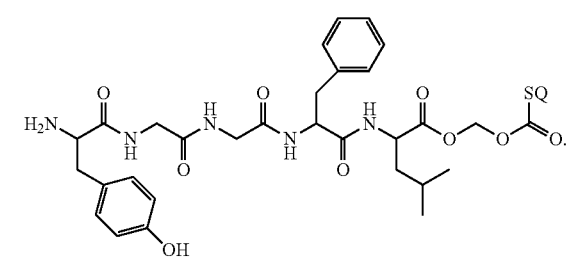

11. The bioconjugate according to claim 1 for use as a drug.

12. The bioconjugate according to claim 1 for use in the treatment of pain disorders.

13. A pharmaceutical composition comprising a bioconjugate comprising at least one neuropeptide covalently bond to at least one hydrocarbon compound of squalene structure (SQ), as represented as follows, (SQ)

wherein:
m1 is 0,1,2,3,4,5,6,7,8, or 9, and
m2 is 0,1,2,3,4,5,6,7,8, or 9,
and wherein

represents the bond to the at least one neuropeptide, and
wherein the at least one neuropeptide has a C-terminal acid covalently bonded to the at least one hydrocarbon compound of squalene structure by using a dioxycarbonyl spacer or the at least one neuropeptide has a N-terminal amine covalently bonded to the at least one hydrocarbon compound of squalene structure by using a diglycolate spacer,
as an active substance, and at least one pharmaceutically acceptable excipient and/or carrier.

14. The pharmaceutical composition according to claim 13 for use in the treatment of pain disorders.

15. A nanoparticle comprising the bioconjugate according to claim 1.

16. The nanoparticle according to claim 15, wherein the nanoparticle further comprises an anti-inflammatory compound.

17. The nanoparticle according to claim 15, wherein the nanoparticle has a mean diameter between 10 and 500 nm.

18. A process for the preparation of a nanoparticle according to claim 15, the process comprising at least:
dispersion of the bioconjugate in at least one organic solvent at a concentration sufficient to obtain, on adding the corresponding mixture, with stirring, to an aqueous phase, instantaneous formation of nanoparticles in suspension in said aqueous phase, and
isolation of said nanoparticles.

19. A patch comprising a bioconjugate of claim 1 optionally in a form of a nanoparticle.

20. The patch according to claim 19, wherein the patch is a patch equipped with micro-needles.

21. The patch according to claim 19 for use in the treatment of pain disorders.

* * * * *